United States Patent
Roorda et al.

(10) Patent No.: US 11,977,070 B2
(45) Date of Patent: May 7, 2024

(54) METHOD AND SYSTEMS FOR PULLING DNA, RNA AND OTHER BIOLOGICAL MOLECULES THROUGH NANOPORES USING SOFT MAGNETIC STRUCTURES

(71) Applicant: UNIVERSAL SEQUENCING TECHNOLOGY CORPORATION DBA UST CORPORATION, Canton, MA (US)

(72) Inventors: Robert Roorda, Hingham, MA (US); Ming Lei, Sharon, MA (US); Nga Ho, Newton, MA (US)

(73) Assignee: Universal Sequencing Technology Corporation, Canton, MA (US)

( * ) Notice: Subject to any disclaimer, the term of this patent is extended or adjusted under 35 U.S.C. 154(b) by 238 days.

(21) Appl. No.: 16/613,016

(22) PCT Filed: May 11, 2018

(86) PCT No.: PCT/US2018/032399
§ 371 (c)(1),
(2) Date: Nov. 12, 2019

(87) PCT Pub. No.: WO2018/209286
PCT Pub. Date: Nov. 15, 2018

(65) Prior Publication Data
US 2020/0096493 A1   Mar. 26, 2020

Related U.S. Application Data

(60) Provisional application No. 62/505,574, filed on May 12, 2017.

(51) Int. Cl.
*C12Q 1/68* (2018.01)
*C12Q 1/6869* (2018.01)
*G01N 33/487* (2006.01)

(52) U.S. Cl.
CPC ..... *G01N 33/48721* (2013.01); *C12Q 1/6869* (2013.01)

(58) Field of Classification Search
CPC ....................................................... C12Q 1/68
(Continued)

(56) References Cited

U.S. PATENT DOCUMENTS 8,449,838 B2   5/2013   Shaikh et al.
2004/0009614 A1 *  1/2004   Ahn .................. B03C 1/00
                                                              436/526

(Continued)

FOREIGN PATENT DOCUMENTS

WO   2017074658 A1   5/2017
WO   2017075620 A1   5/2017

OTHER PUBLICATIONS

International Search Report and Written Opinion of the International Searching Authority, PCT/US2018/032399 dated Jul. 30, 2018, 10 pages.

(Continued)

*Primary Examiner* — Aaron A Priest
(74) *Attorney, Agent, or Firm* — Melissa Hunter-Ensor; Nathan Hsu; Greenberg Traurig, LLP

(57) ABSTRACT

The present disclosure relates generally to methods of controlling the movement of molecules, such as DNA (Deoxyribonucleic Acid), RNA (Ribonucleic Acid) and proteins as well as other biological molecules passing through nanopores. In particular, the disclosure describes how structures made of soft magnetic material can be used to selectively hold, pull and release DNA tagged with magnetic beads.

31 Claims, 22 Drawing Sheets

500: nanopore
501: nanopore chip
510: scan plate
511: soft magnet array
520: controllable magnet
522: magnetic field
523: strong local field depth
530: electrical bias source
570: analysis stage
571: Separation distance
600: DNA to be analyzed
601: linker node
602: flexible linker molecule
610: scan plate attachment
620: magnetic bead Automatic alignment with magnetic beads

(58) Field of Classification Search
USPC .......................................................... 435/6.1
See application file for complete search history.

(56) References Cited

U.S. PATENT DOCUMENTS

| | | | | |
|---|---|---|---|---|
| 2005/0136408 | A1* | 6/2005 | Tom-Moy | C12Q 1/6816 |
| | | | | 435/6.12 |
| 2006/0063171 | A1* | 3/2006 | Akeson | G01N 33/48721 |
| | | | | 435/6.11 |
| 2010/0084276 | A1 | 4/2010 | Lindsay | |
| 2010/0331194 | A1* | 12/2010 | Turner | G01N 27/44791 |
| | | | | 506/2 |
| 2013/0146457 | A1* | 6/2013 | Gundlach | C07K 14/35 |
| | | | | 204/451 |
| 2014/0199209 | A1* | 7/2014 | Chan | C12Q 1/6869 |
| | | | | 422/82.08 |
| 2017/0268054 | A1* | 9/2017 | Akahori | G01N 33/48721 |
| 2019/0256905 | A1* | 8/2019 | Jawaharlal | G01R 33/12 |

OTHER PUBLICATIONS

Peng, et al., "Reverse DNA translocation through a solid-state nanopore by magnetic tweezers" Nanotechnology. 2009; 20(8): 185101 (doi: 10.1088/0957-4484/20/18/185101).

Keyser, et al., "Direct force measurements on DNA in a solid-state nanopore", Nature Physics, 2006: 2:473-477 (doi: 10.1038/nphys344).

Smistrup, K., Hansen, M. F., Bruus, H., Tang, P. T., & Kruhne, U. W. W. (2007). Magnetic separation in microfluidic systems.

Meeker, D. "Finite Element Method Magnetic", Software, version 4.2.

European Patent Office Search Report, EP 18799201.1, dated Feb. 8, 2021, 8 pages.

* cited by examiner

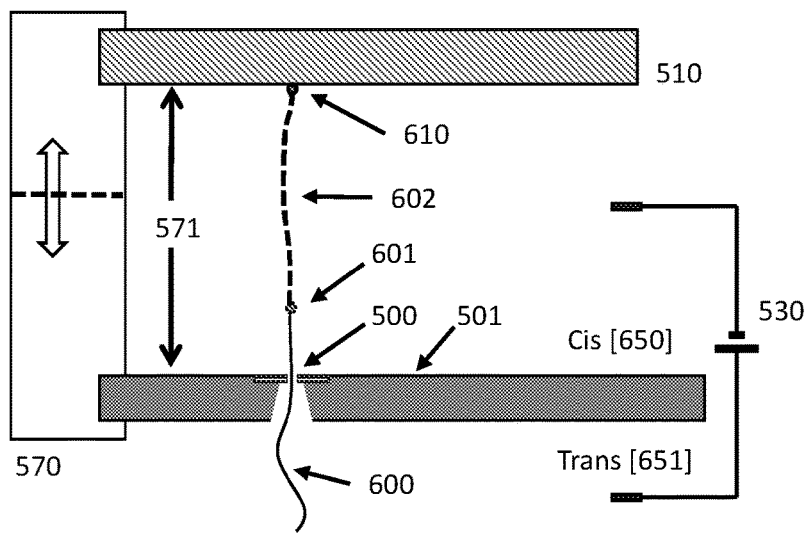
FIG. 1: General layout
(copied from PCT/US16/59794 Lei et al, Fig#1)

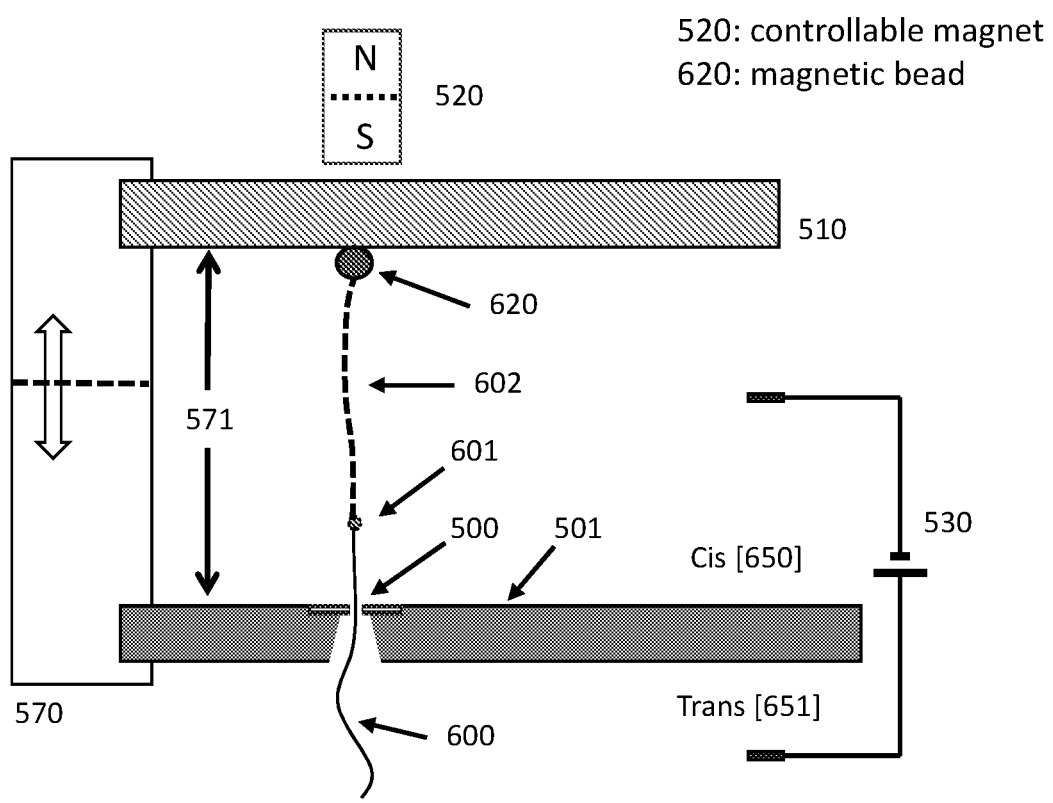
FIG. 2: Automatic alignment with magnetic beads
(copied from PCT/US16/59794 Lei et al Fig#12)

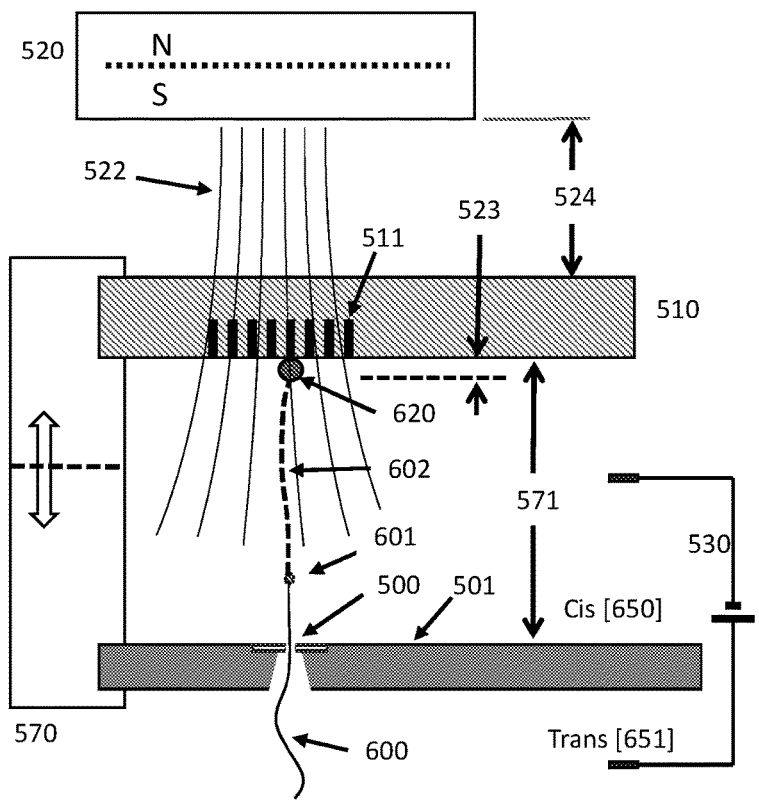
FIG. 3: Automatic alignment with magnetic beads

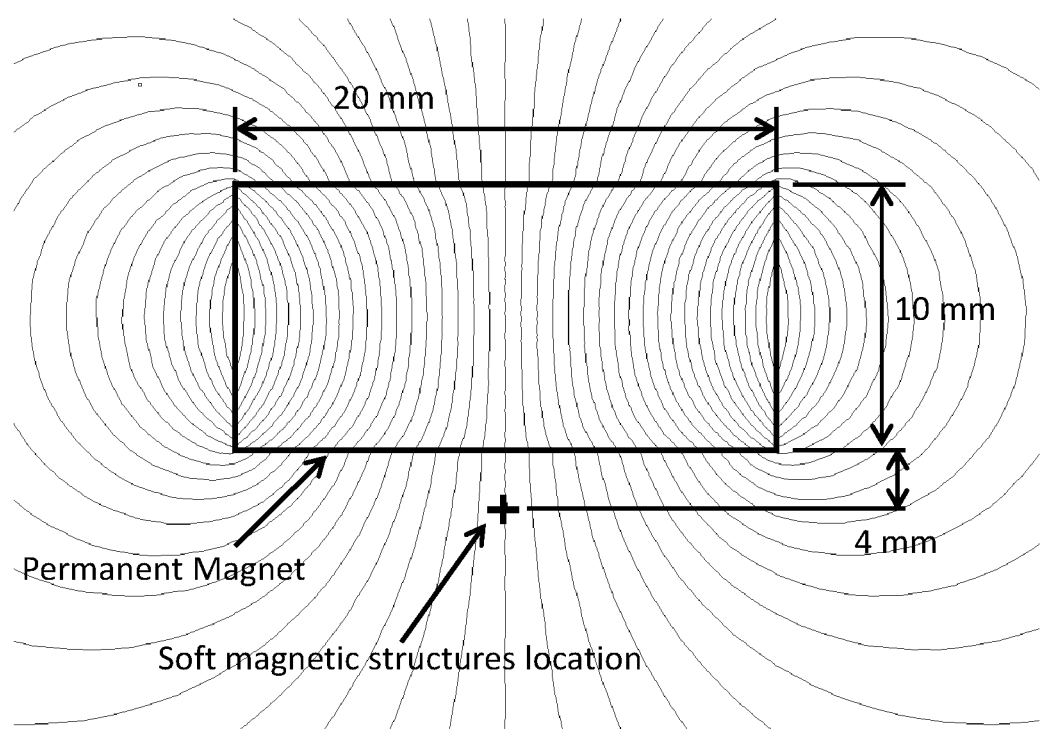
FIG. 4: Diagram of Rectangular FEMM layout.

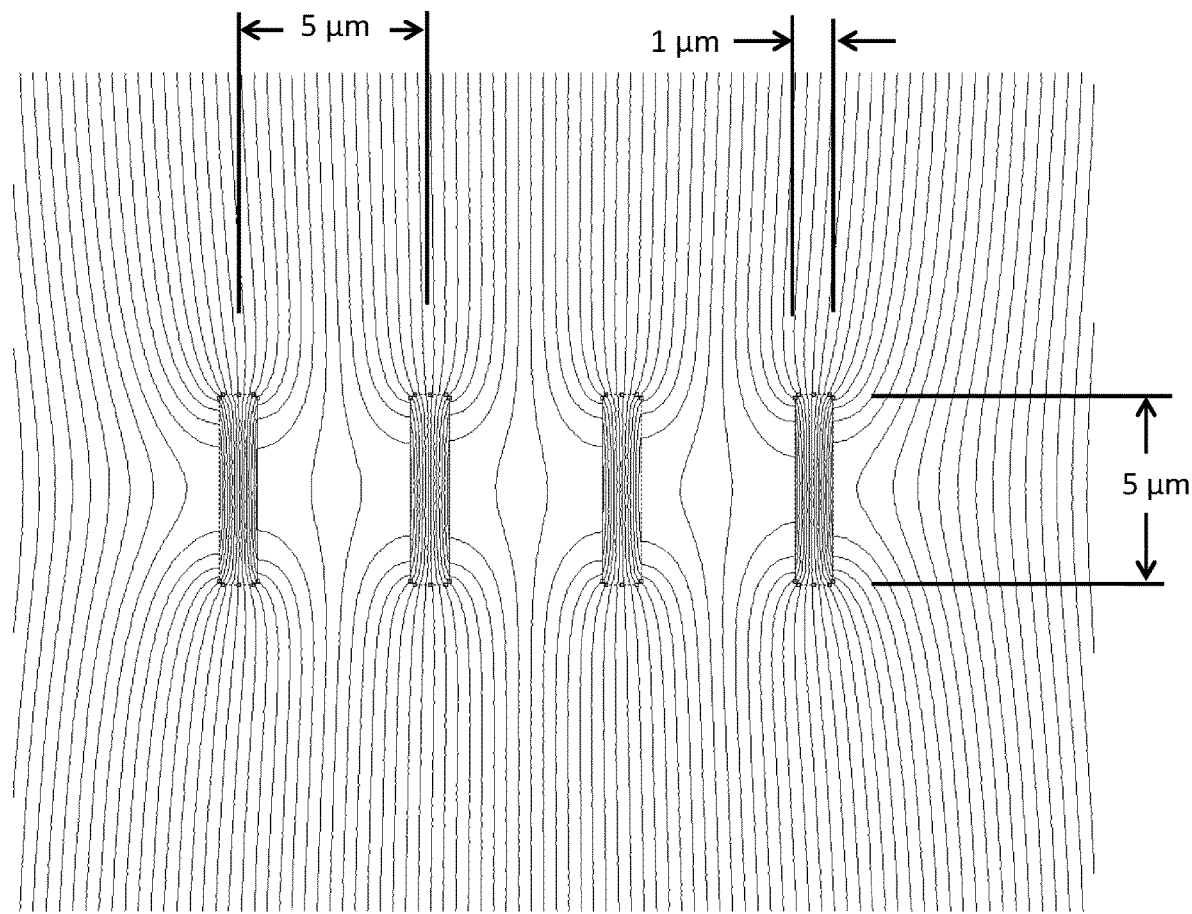
FIG. 5: Magnetic flux near soft magnetic structures

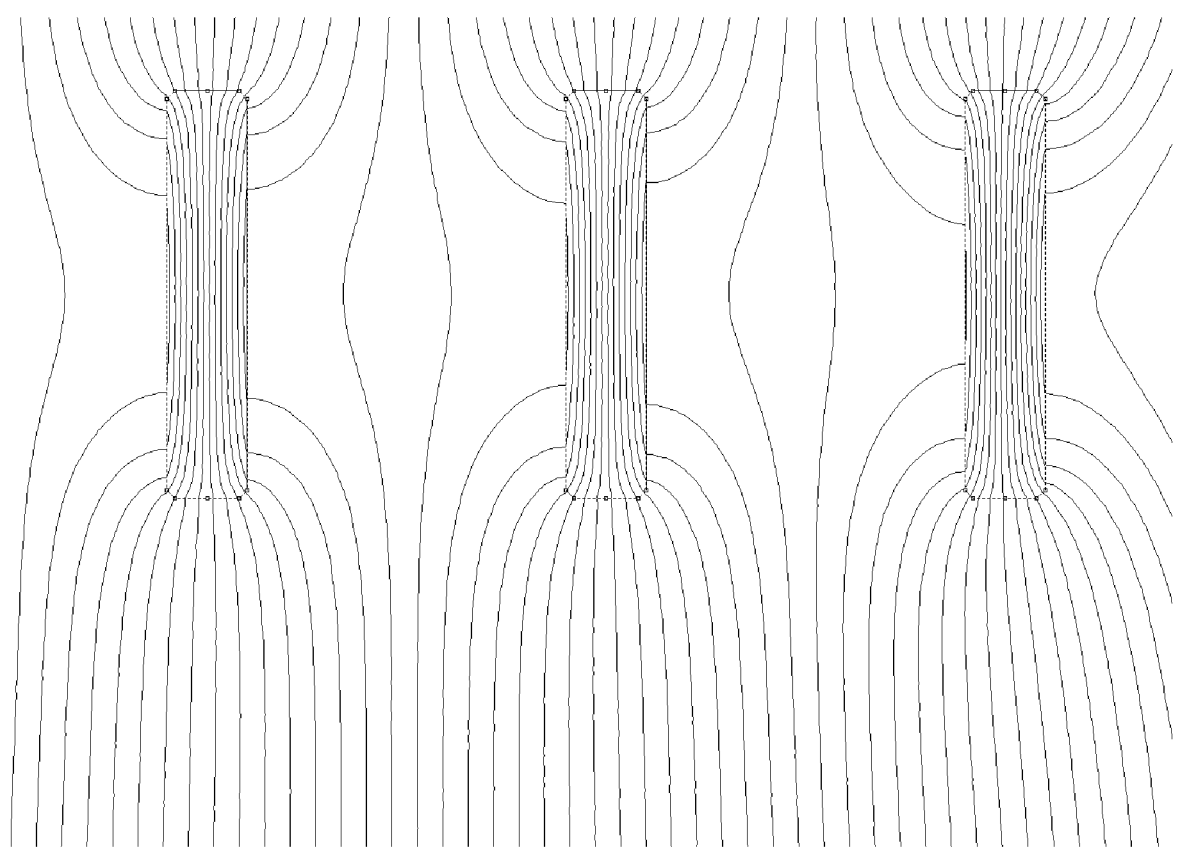
FIG. 6: Magnetic flux near poles of soft magnetic structures

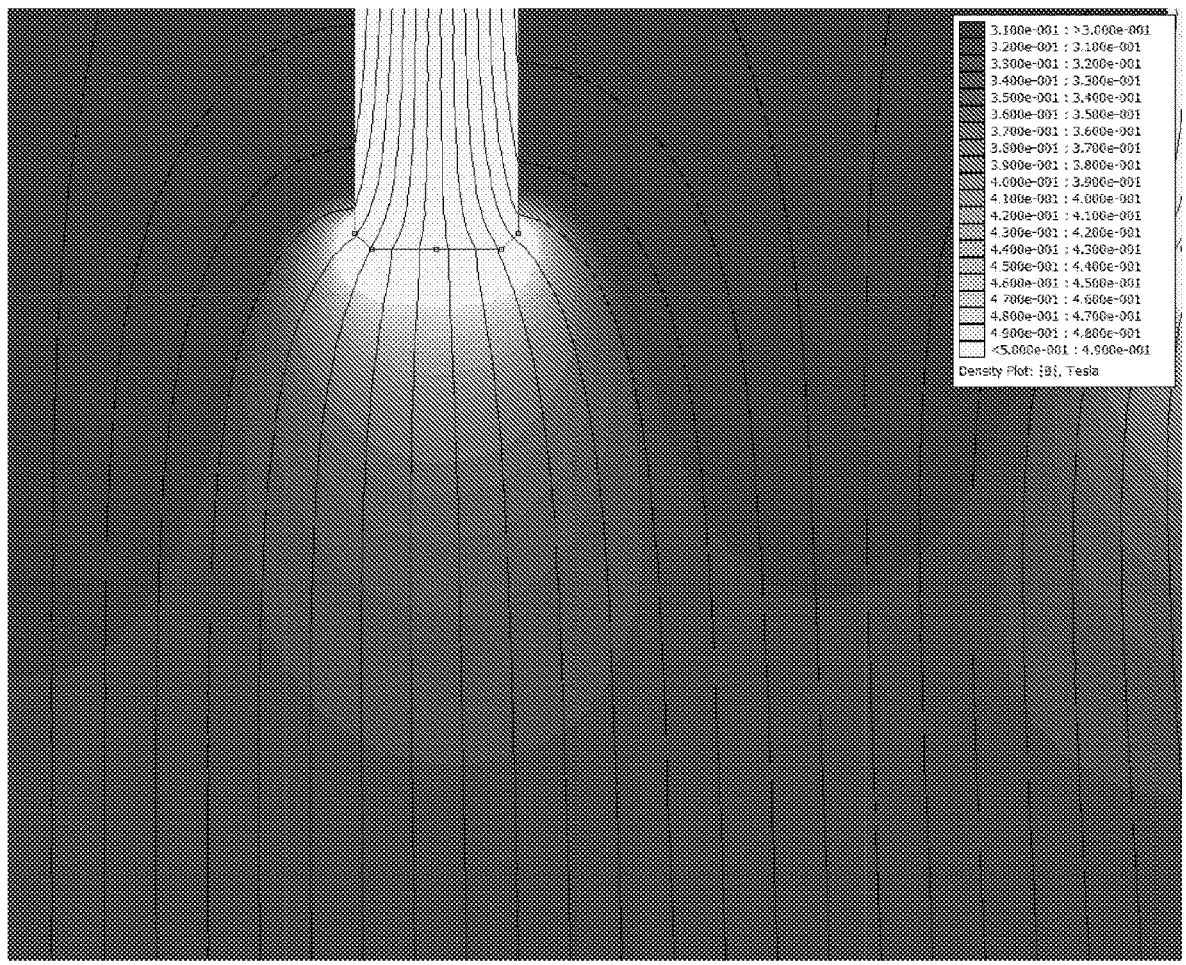
FIG. 7: Magnetic flux and magnetic field strength near soft magnetic structure end.

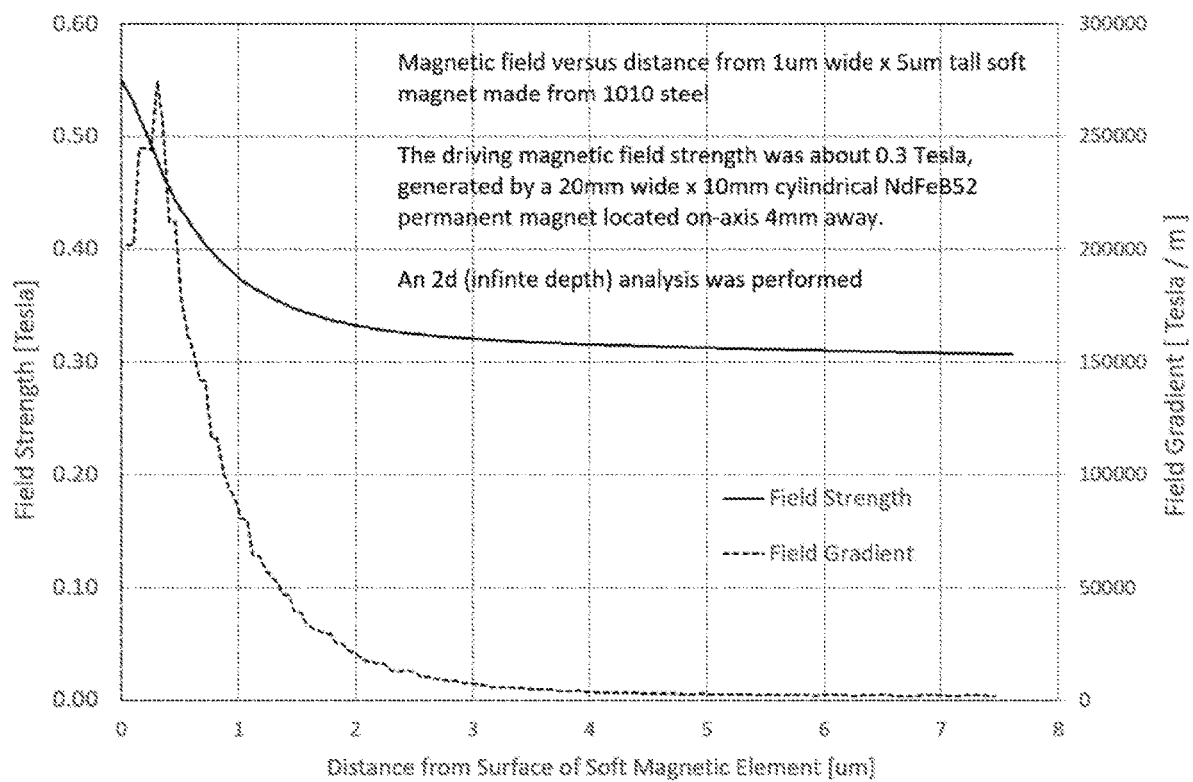
FIG. 8: Graph of magnetic field strength and field gradient modeled along a vertical line below the end of the soft magnetic structure

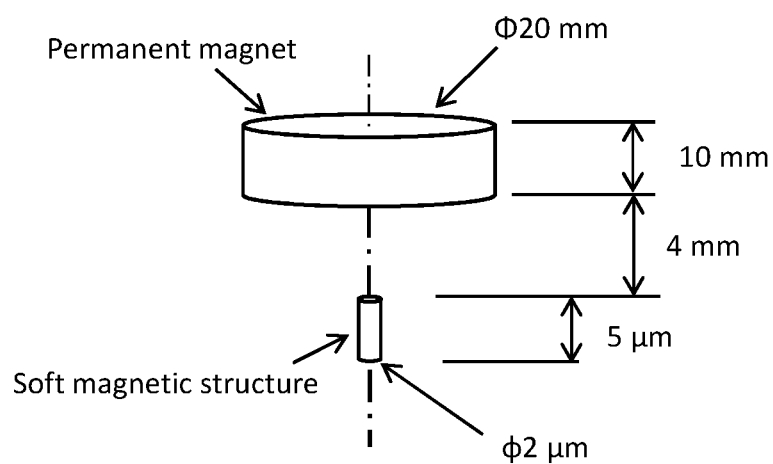
(NOT TO SCALE)
FIG. 9: Illustration of FEMM physical model

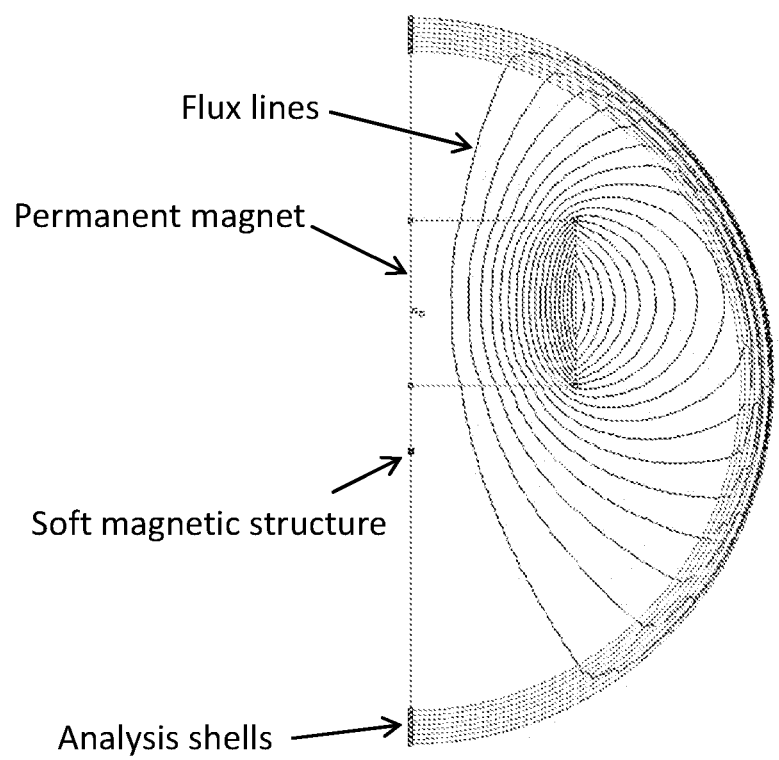
FIG. 10: Illustration of axial-symmetric physical model showing field lines

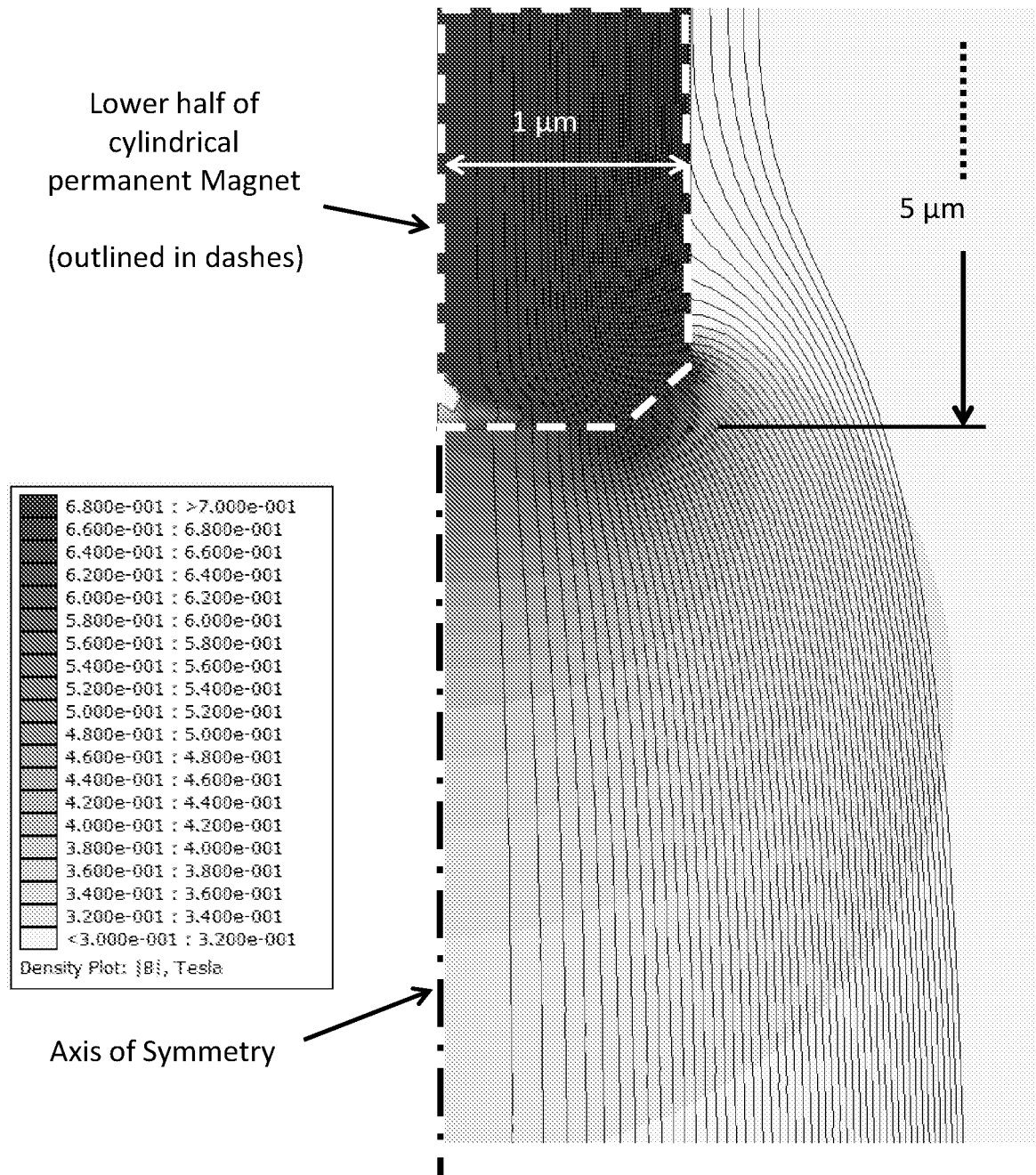
FIG. 11: Close up on the flux near end of cylindrical soft magnetic structure.

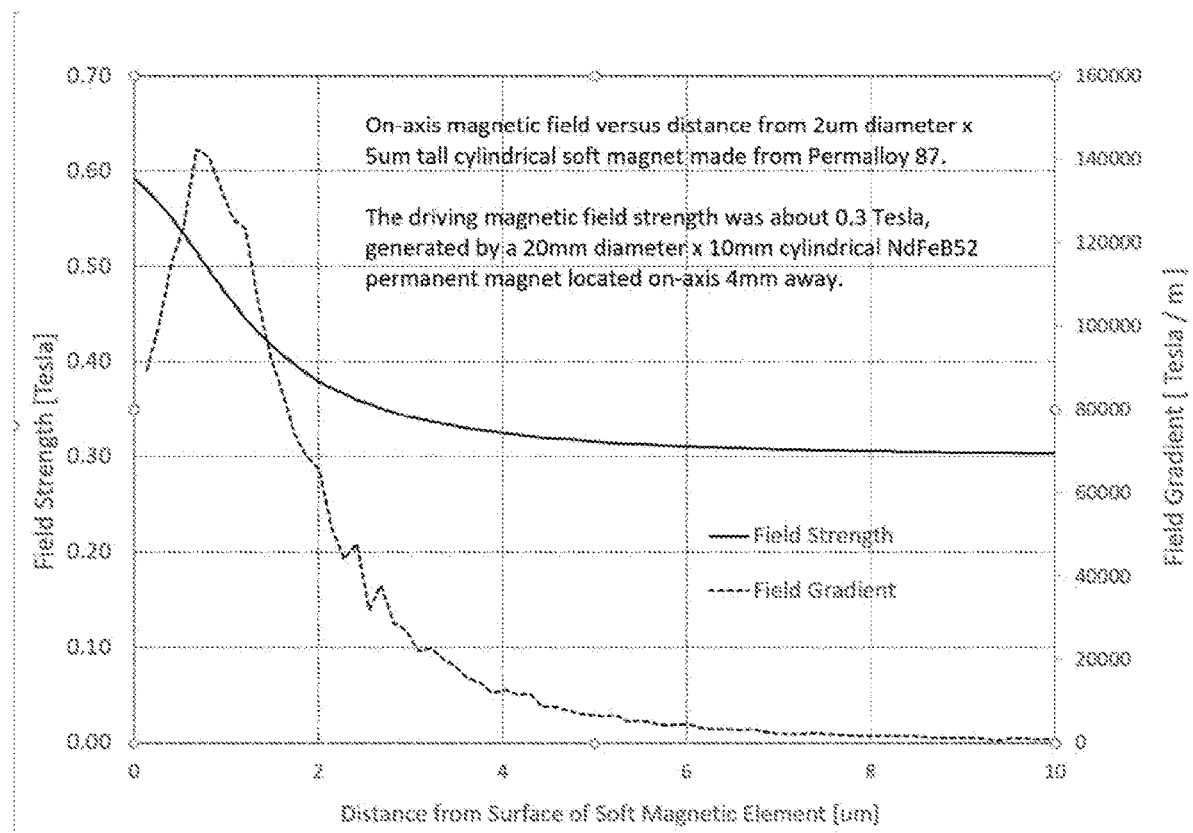
FIG. 12: Graph of magnetic field strength and field gradient modeled along a vertical line below the end of the soft magnetic structure.

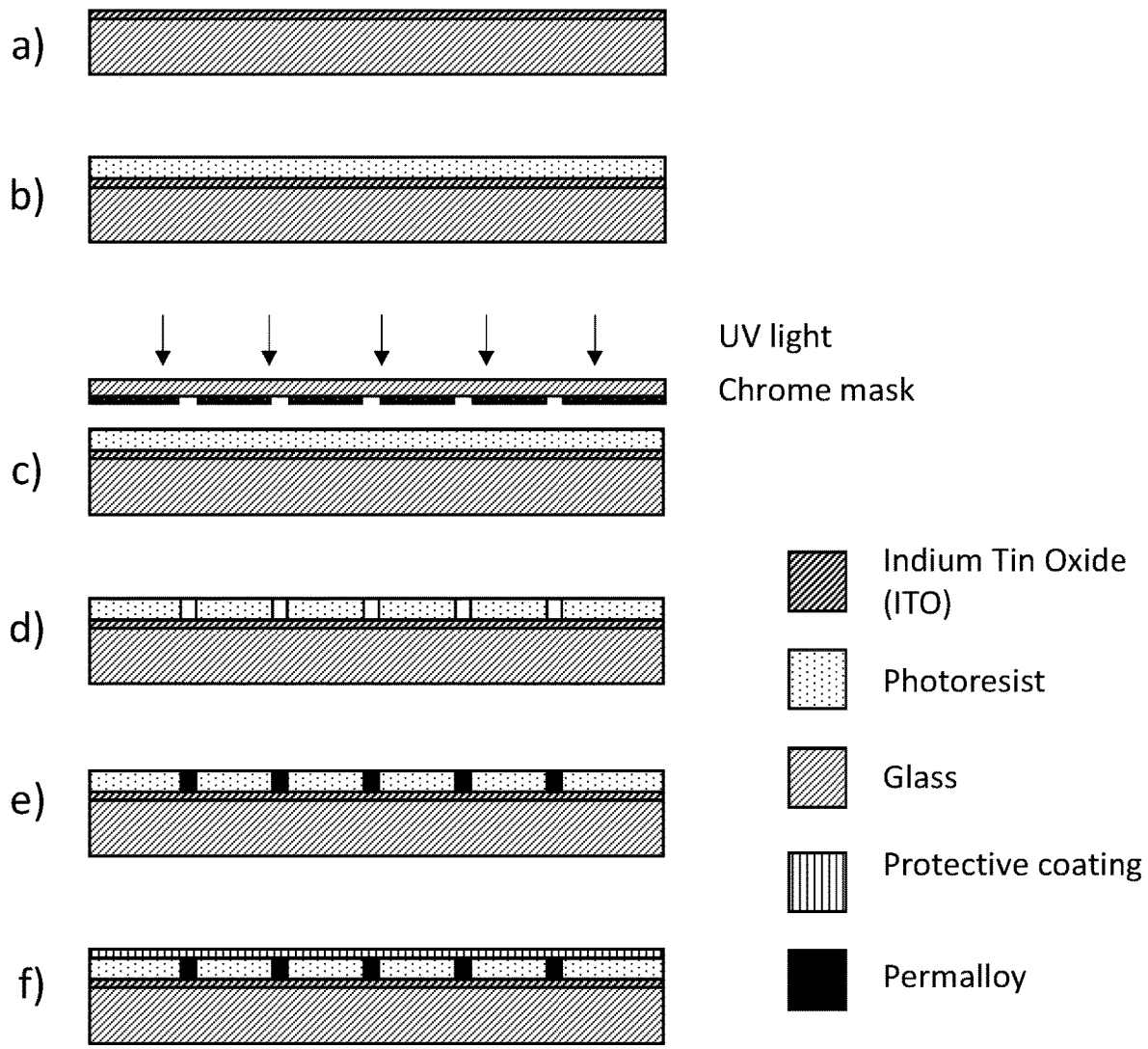
FIG. 13: Scan plate fabrication process

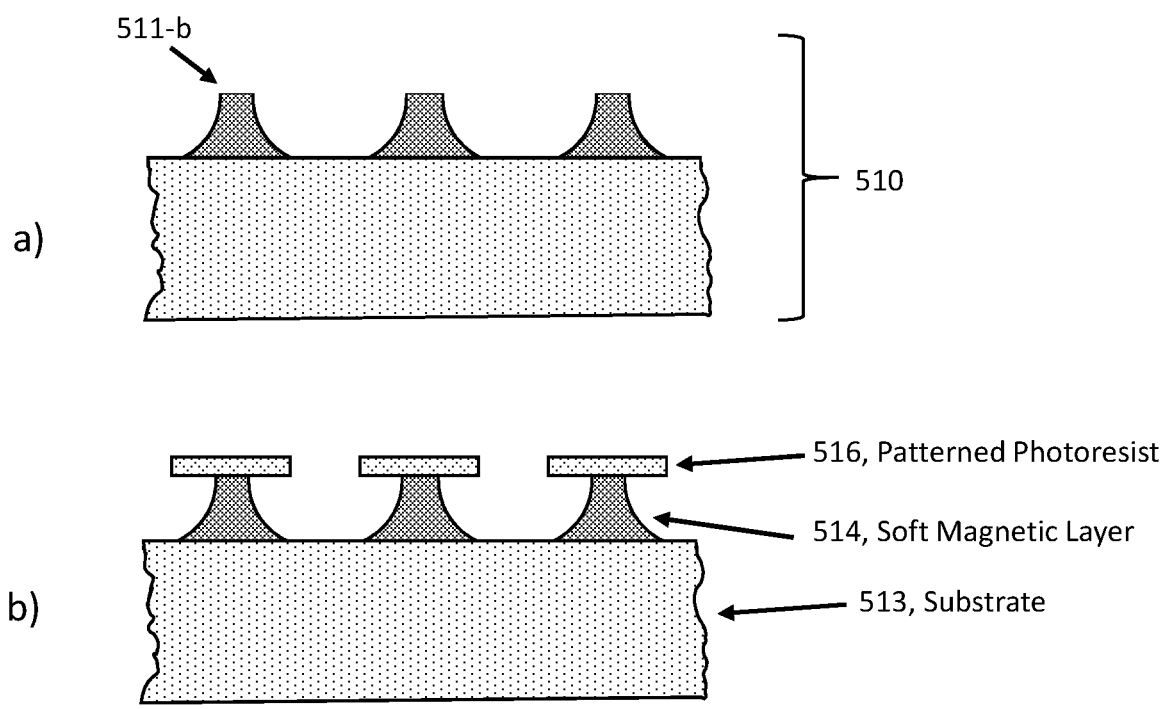
FIG. 14: Cross-section of soft magnetic structures that protrude above the surface of the scan plate

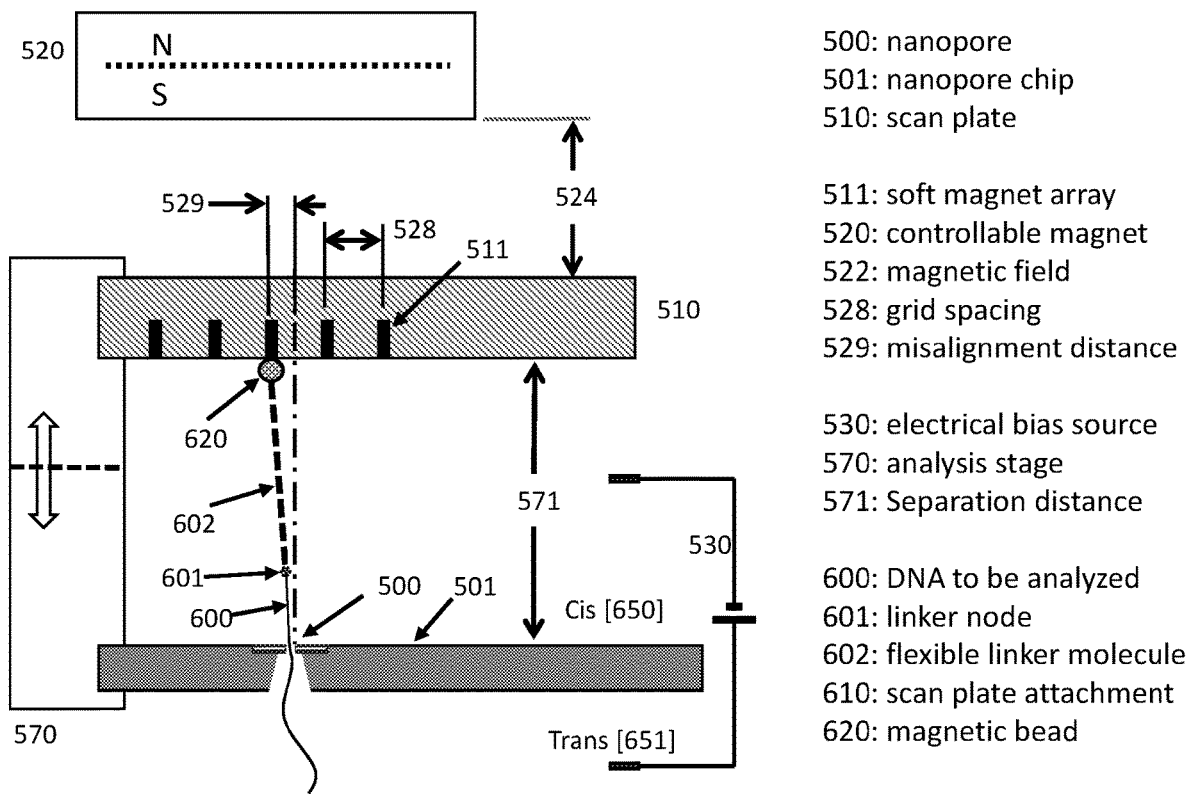
FIG. 15: Illustration of DNA misalignment.

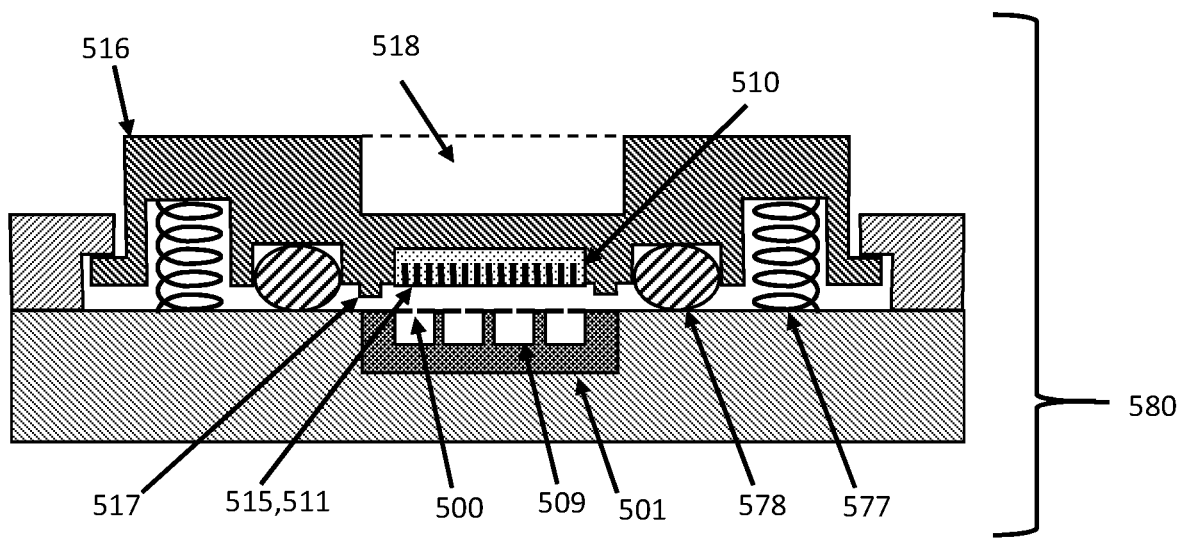
500: nanopore
509: isolated nanopore well
515: scan plate bottom surface
517: separation shim
578: seal
518: clearance for controllable magnet
580: dynamic chamber subassembly with springs and seals
501: nanopore chip
510: scan plate
511: soft magnetic structures
577: compression spring
516: scan plate mount
FIG. 16: Dynamic chamber with soft magnetic structures and assessible scan plate.

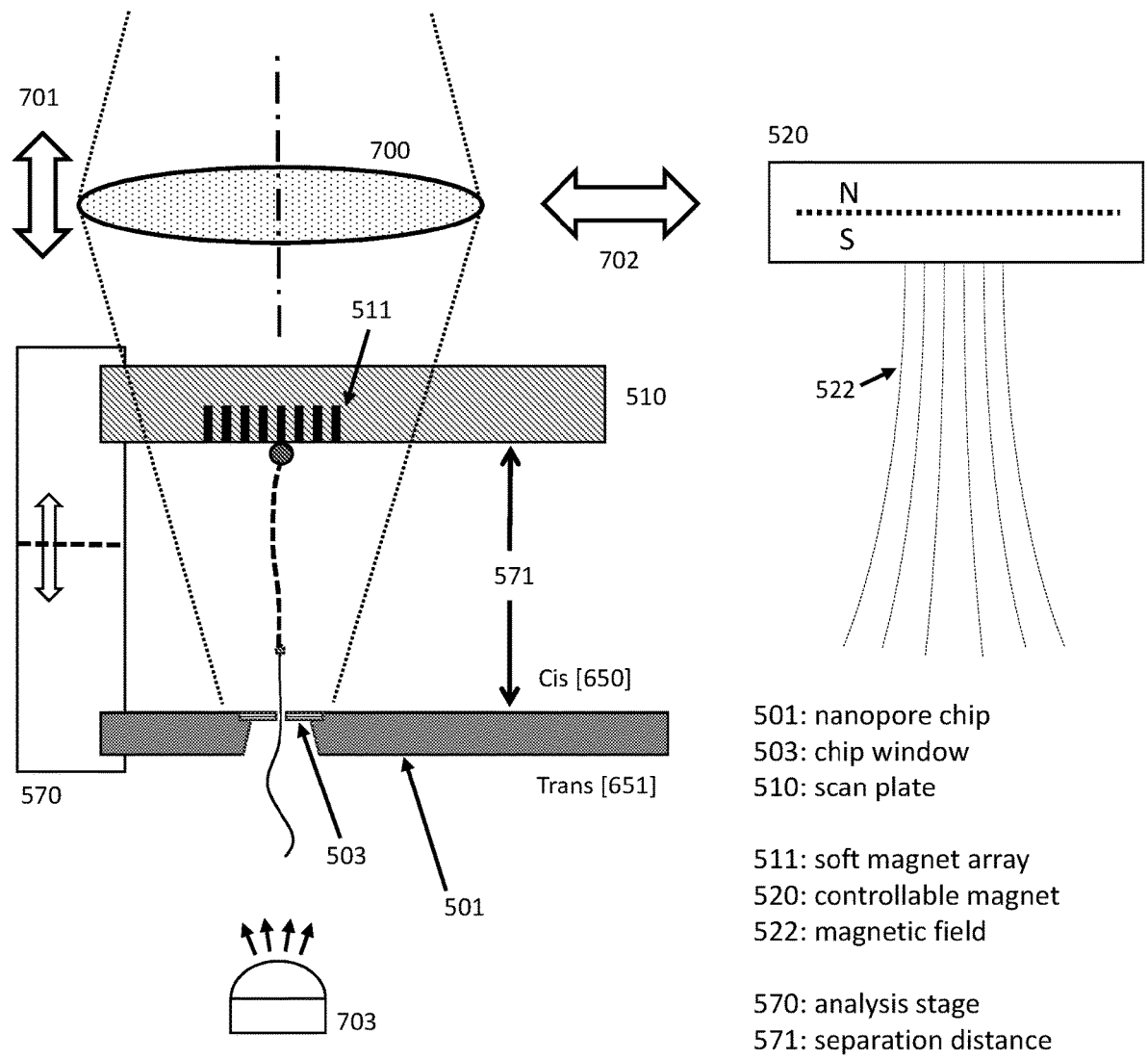
FIG. 17: Optical position feedback
501: nanopore chip
503: chip window
510: scan plate
511: soft magnet array
520: controllable magnet
522: magnetic field
570: analysis stage
571: separation distance
700: lens
701: lens focusing
702: magnet/Lens exchange
703: transmitted light source

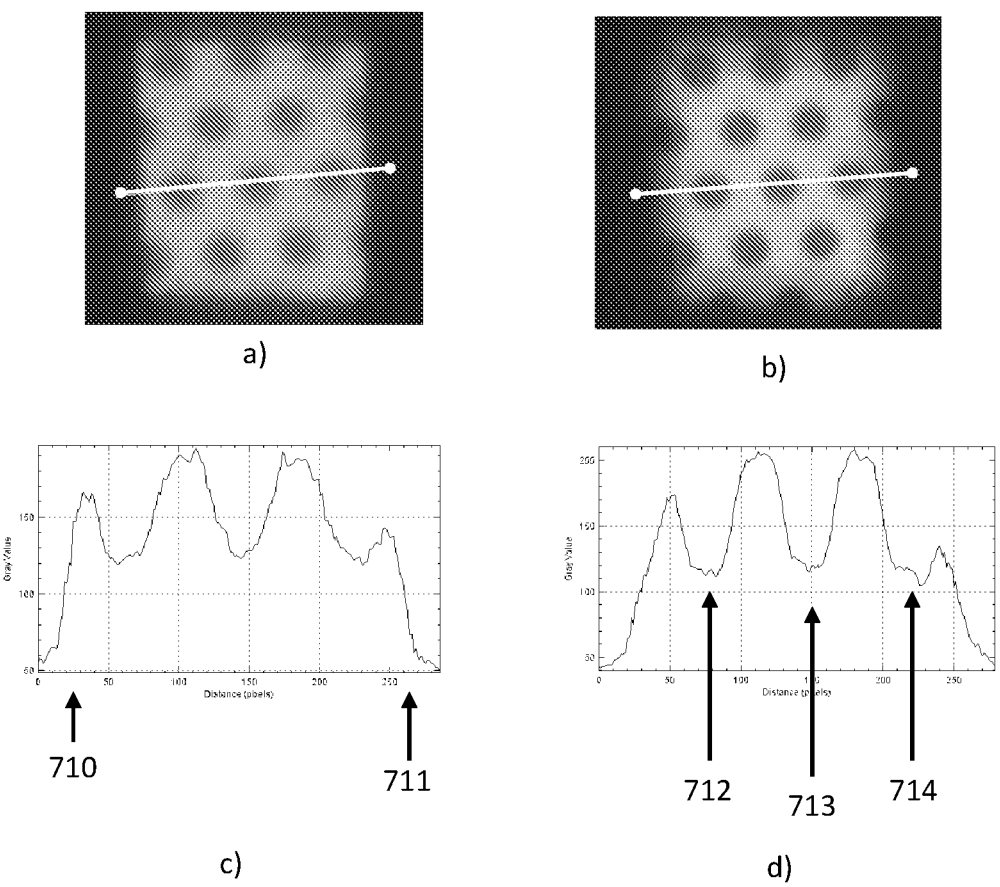
FIG. 18: Images of a nanopore chip window captured through the scanplate

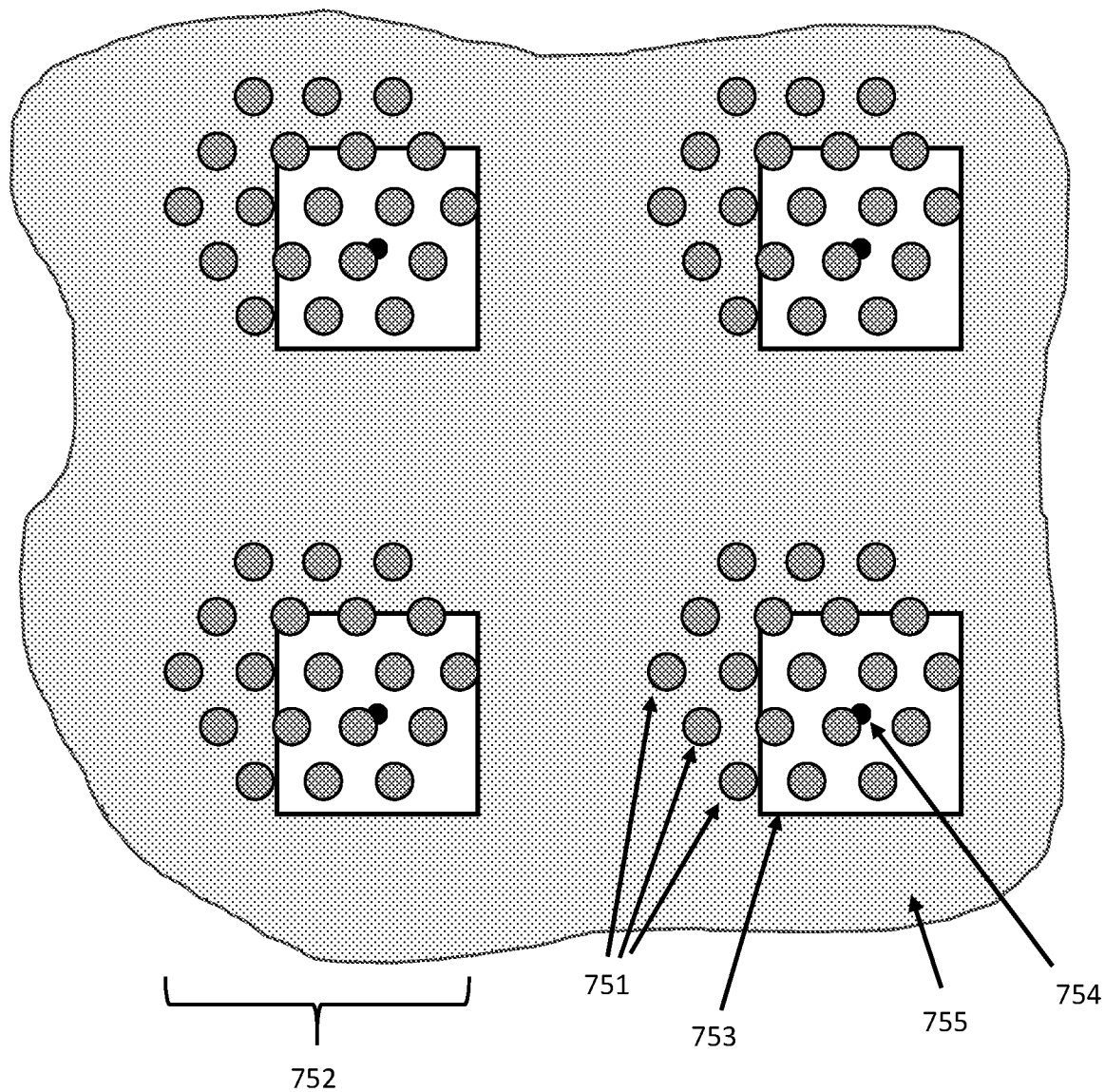
751: Soft magnetic material structures
752: Cluster of 19 soft magnetic material structures
755: Substrate
753: Thinned window in substrate
754: Nanopore
FIG. 19: Illustration of clusters of soft magnetic material structures which are closely aligned with specific nanopores on a substrate.

| On Axis Magnetic Field Measurements [Tesla] | | | | | | | |
|---|---|---|---|---|---|---|---|
| distance [mm] | bullet #1 | bullet #2 | cylinder | cone 0.5"dia | cone 1.0" | Pyramid 1.0" | Pyramid+Cyl |
| 0 | 0.619 | 0.6 | 0.358 | 0.633 | 0.694 | 0.889 | 0.742 |
| 0.1 | 0.581 | 0.575 | 0.339 | 0.57 | 0.631 | 0.845 | 0.718 |
| 0.2 | 0.513 | 0.513 | 0.278 | 0.513 | 0.58 | 0.805 | 0.673 |
| 0.3 | 0.457 | 0.46 | 0.232 | 0.465 | 0.534 | 0.761 | 0.632 |
| 0.4 | 0.41 | 0.414 | 0.195 | 0.426 | 0.494 | 0.725 | 0.593 |
| 0.5 | 0.37 | 0.374 | 0.165 | 0.391 | 0.461 | 0.688 | 0.556 |
| 0.6 | 0.336 | 0.341 | 0.141 | 0.361 | 0.432 | 0.654 | 0.522 |

FIG. 20A: Magnetic Field Measurements

| On-Axis Magnetic Field Gradients [Tesla/m] | | | | | | | |
|---|---|---|---|---|---|---|---|
| distance [mm] | bullet #1 | bullet #2 | cylinder | cone 0.5"dia | cone 1.0" | Pyramid 1.0" | Pyramid+Cyl |
| 0.05 | 380 | 250 | 190 | 630 | 630 | 440 | 240 |
| 0.15 | 680 | 620 | 610 | 570 | 510 | 400 | 450 |
| 0.25 | 560 | 530 | 460 | 480 | 460 | 440 | 410 |
| 0.35 | 470 | 460 | 370 | 390 | 400 | 360 | 390 |
| 0.45 | 400 | 400 | 300 | 350 | 330 | 370 | 370 |
| 0.55 | 340 | 330 | 240 | 300 | 290 | 340 | 340 |

FIG. 20B: Magnetic Field Gradients

| Calculation of the force a magnet exerts on a bead. | | | |
|---|---|---|---|
| 8/23/2016 | | | |
| Bead ID | 1.05 um Dynabeads | | |
| Bead diameter | 1.05 | um | |
| | 0.00000105 | m | |
| bead volume | 6.1E-19 | m^3 | 4/3*pi*r^3 |
| Field Gradient | 450 | T/m | from experiments |
| Max Field | 2700 | Gauss | from experiments |
| | 214860.6 | A/m | (x 79.578) |
| (The max field >60000 and therefore the bead is saturated) | | | |
| Saturated Bead Magnetisation | 3.00E+04 | A/m | measured, Smistrup 2007 |
| Force | 8.18E-12 | N | Volume * MagSat * Gradient |
| | 0.00 | Kg*m* s^-2 | |
| | 8.18 | pN | |

FIG 21: Magnetic Force Calculation

|  | Lateral Mis-alignment [µm] | | | | | |
| --- | --- | --- | --- | --- | --- | --- |
|  | 0 | 1 | 2 | 3 | 5 | 10 |
| Plate Distance [µm] | DNA Motion [µm] per 1 µm plate movement | | | | | |
| 5 | 1.000 | 0.976 | 0.913 | 0.831 | 0.668 | 0.410 |
| 10 | 1.000 | 0.994 | 0.978 | 0.953 | 0.885 | 0.689 |
| 15 | 1.000 | 0.998 | 0.991 | 0.979 | 0.945 | 0.823 |
| 20 | 1.000 | 0.999 | 0.995 | 0.988 | 0.969 | 0.890 |
| 25 | 1.000 | 0.999 | 0.997 | 0.993 | 0.980 | 0.926 |
| 30 | 1.000 | 0.999 | 0.998 | 0.995 | 0.986 | 0.947 |
| 35 | 1.000 | 1.000 | 0.998 | 0.996 | 0.990 | 0.960 |
| 40 | 1.000 | 1.000 | 0.999 | 0.997 | 0.992 | 0.969 |

FIG. 22: DNA pulling speed reduction factor calculation.

METHOD AND SYSTEMS FOR PULLING DNA, RNA AND OTHER BIOLOGICAL MOLECULES THROUGH NANOPORES USING SOFT MAGNETIC STRUCTURES

SUMMARY/ABSTRACT

The present disclosure relates generally to methods of controlling the movement of molecules, such as DNA (Deoxyribonucleic Acid), RNA (Ribonucleic Acid) and proteins as well as other biological molecules passing through nanopores.

It specifically describes the method of using structures made of soft magnetic material to selectively hold, pull and release DNA tagged with magnetic beads.

BACKGROUND

Throughout this disclosure although the manipulation of DNA is described. These methods can be generalized to RNA and other charged linear molecules.

Nanopore technology has the potential to provide accurate, long read length genetic information by identifying nucleotides as a DNA is pulled through a nanopore. Controlling the progression of DNA through a nanopore at a slow and steady rate is critical to perform accurate sequencing.

Patent application PCT/US16/59794, Lei et al., the subject matter of which is herein incorporated by reference in its entirety, describes methods for realizing this control. The present disclosure improves upon those methods.

BRIEF SUMMARY OF PCT/US16/59794, LEI ET AL

Lei et al. describes a means of pulling a strand of DNA through a nanopore with good control of the translocation speed of the DNA. The DNA is pulled through the nanopore by the voltage bias of the nanopore acting on the charged backbone of the DNA molecule. The DNA is pulled from the cis side of the nanopore to the trans side. "cis" and "trans" refer to the mutually isolated spaces on the originating and receiving sides of the nanopore orifice respectively. On the cis side, the exposed end of the DNA is attached to a scan plate. The attachment can be made by permanent means such as covalent bonding or by non-permanent means such as tagging with magnetic beads. The DNA is stretched between the scan plate and the nanopore. The tension in the DNA is determined by the pulling of the electric field within the nanopore which is proportional to the voltage bias (i.e. potential difference) across the nanopore. The separation distance between the nanopore and the scan plate is controlled by a precise mechanical actuator, typically by a piezo electric device with nanometer precision. By increasing the separation distance the stretched DNA is pulled through the nanopore under constant tension. By decreasing the separation distance the stretched DNA is drawn into the nanopore under constant tension. By holding the DNA under constant tension the translocation rate is well controlled and the effect of Brownian motion is reduced.

PCT/US16/59794 Lei et al further discloses a method of "Automatic alignment of DNA". This method utilizes a controllable magnet to attract, hold, pull and release magnetic beads tagged with DNA during a sequencing procedure.

The disclosure explains that the force on a magnetic bead is determined by the volume of the bead, its magnetization, and by the gradient of the magnetic field:

Force Acting on a Magnetic Bead

The force of a magnet acting on a volume of magnetic material such as a magnetic bead, $\vec{F}_m$ is roughly proportional to the gradient of the magnetic field $\vec{H}_0$, the magnetization of the material $\vec{M}$, and the volume of the magnetic material in the bead $V_{BEAD}$ as given by the formulas below.

$$\vec{F}_m = \mu_0 * V_{BEAD} * (\vec{M} \cdot \nabla) \vec{H}_0 \text{(complete formula)}$$

For strong magnetic fields the magnetization of the magnetic beads approaches its saturation limit and is no longer proportional to the driving magnetic field. The force formula can be simplified to:

$$\vec{F}_m \approx V_{BEAD} * M_{saturation} * \vec{G} \text{(simplified formula for saturated magnetic materials)}$$

Where:

$M_{SATURATION}$ is the bead magnetization at saturation $\vec{G}$ is the gradient of the magnetic field.

Strong force is desirable since this enables increasing the tension in the DNA by raising the nanopore bias voltage. If the retention force is weak the magnetic bead will fall off the scan plate when the DNA is pulled by a large bias voltage.

Invention Summary

This invention is a means by which DNA tagged with magnetic beads can be pulled through a nanopore while being held by very strong electrostatic forces. The invention uses small soft magnetic structures to create extremely large magnetic field gradients that trap the magnetic beads against a scan plate that can be moved with nanometer precision.

With this approach the magnetic trapping force can be increase by several orders of magnitude compared to what is possible with conventional magnets. The DNA tension can therefore be increased for better control of the DNA progression through the nanopore. For clarity, the soft magnetic structure is not a magnet, but a structure that can alter the magnetic field significantly when placed in the magnetic field generated by a magnet.

BRIEF DESCRIPTION OF FIGURES

FIG. 1: General layout. This is a copy of a figure from the patent application PCT/US16/59794 Lei et al which illustrates a mechanical assembly for DNA sequencing.

FIG. 2: Automatic alignment with magnetic beads. This is a copy of a figure from the patent application PCT/US16/59794 Lei et al which illustrates a method for aligning DNA tagged with a magnetic bead such that it can be pulled straight above a nanopore.

FIG. 3: Automatic alignment with magnetic beads. This illustrates the present invention. A mechanical assembly is depicted including soft magnetic structures positioned superficially on the side of a scan plate facing a nanopore chip. A permanent magnet is depicted positioned such that magnetic flux penetrates the soft magnetic structures.

FIG. 4: diagram of rectangular FEMM layout. This illustrates the physical layout of a 2-dimensional finite element analysis model analysis.

FIG. 5: magnetic flux near soft magnetic structures. The magnetic flux near a 4×1 array of soft magnetic structures was calculated with a 2d FEA analysis and is shown with dimensions overlaid.

FIG. 6: magnetic flux near poles of soft magnetic structures. The magnetic flux near a 4×1 array of soft magnetic structures was calculated with a 2d FEA analysis. The portion of that analysis immediately near the poles of the soft magnetic structures is presented.

FIG. 7 shows the flux lines as solid lines and the field strength as grayscales.

FIG. 8: graph of magnetic field strength and field gradient modeled alone a vertical line below the end of the soft magnetic structure. Results for 2d FEA analysis.

FIG. 9: Illustration of FEMM physical model. This illustrates the layout of the 3d axially-symmetric FEA model used to analyze cylindrical soft magnetic structures.

FIG. 10: Illustration of axial-symmetric physical model showing field lines. This illustrates the 2d cross-section of the 3d axially-symmetric FEA model used to analyze cylindrical soft magnetic structures.

FIG. 11: Close up on the flux near end of cylindrical soft magnetic structure. Close-up view of the magnetic field and flux line output of the 3d axially-symmetric FEA analysis of cylindrical soft magnetic structures.

FIG. 12: Graph of magnetic field strength and field gradient modeled alone a vertical line below the end of the soft magnetic structure. Results from 3d axially-symmetric FEA analysis of cylindrical soft magnetic structures.

FIG. 13: Scan plate fabrication process. The diagrams illustrate the stages of a creating a scan plate with soft magnetic structures using micro-lithography techniques.

FIG. 14: Cross-section of soft magnetic structures that protrude above the surface of the scan plate. These diagrams illustrate a soft magnetic structure that protrudes from the scan plate and how it might be fabricated using micro-lithography techniques.

FIG. 15: Illustration of DNA misalignment. This diagram schematically depicts the misalignment of a magnetic bead due to the spacing of soft magnetic structures.

FIG. 16: Dynamic chamber with soft magnetic structures and assessible scan plate. This depicts how the dynamic chamber design disclosed by patent application PCT/US16/59794 Lei et al can be modified to add soft magnetic structures to the scan plate.

FIG. 17: Optical position feedback. A sequencing assembly is illustrated show how a magnet can be exchanged with an optical system to determine the relative positions of the scan plate and the nanopore chip.

FIG. 18: Images of a nanopore chip window captured through a scan plate. These images and the accompanying graphs of intensity demonstrate how the optical system can determine the separation distance of the scan plate and the nanopore chip.

FIG. 19: Illustration of clusters of soft magnetic material structures. The clusters are closely aligned with specific nanopores on a substrate.

FIGS. 20A and 20B: Magnetic field measurements. Magnetic field measurements were taken for various permanent magnets to evaluate the maximum practical magnetic field gradient that can be used.

FIG. 21: Magnetic force calculation. The maximum magnetic field force was calculated for a commonly used magnetic bead.

FIG. 22: DNA pulling speed reduction factor calculation. The DNA pulling rate was calculated taking into account misalignment of magnetic beads with respect to a nanopore.

DETAILED DESCRIPTION OF INVENTION

The invention greatly increases the force with which magnetic beads can be held against a scan plate for the purpose of pulling DNA and other molecules through a nanopore.

Before explaining at least one embodiment consistent with the present invention in detail, it is to be understood that the invention is not limited in its application to the details of construction and to the arrangements of the objects set forth in the following description or illustrated in the drawings. Methods and apparatuses consistent with the present invention are capable of other embodiments and being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

Further, before turning to the Figures, which illustrate the illustrative embodiments in detail, it should be understood that the present disclosure is not limited to the details or methodology set forth in the description or illustrated in the Figures. It should also be understood that the terminology is for the purpose of description only and should not be regarded as limiting. An effort has been made to use the same.

Estimating the Maximum Force on a Magnetic Bead.

The force can be increased either by increasing the volume of amount of magnetic material, increasing the magnetization of that volume, or by increasing the magnetic field gradient.

Making a magnetic bead larger raises its cost. It also increases its surface area which may result in unwanted adhesion since it increases the number of bonding sites on the bead. Larger beads take up more space as well which may be problematic since it limits the concentration of the DNA.

The magnetization of a bead can be increased somewhat, but high concentrations of iron can retain magnetization in the absence of an external field which leads to clumping. Raising the density also speeds up the settling of beads.

Super-paramagnetic beads retain minimal magnetization and generally have lower density of iron. Small beads are preferred to minimizing cost, and staying in fluid suspension longer.

Increasing the magnetic field gradient is the preferred method for maximizing the force holding/pulling the end of the DNA. In general, permanent magnets are much stronger than electromagnets. FIGS. 20A ad 20B summarize measurements performed to test a number of small but high strength neodymium magnets. These measurements were made using a gaussmeter mounted on a micrometer to measure the magnetic field at different distances from the permanent magnets. The purpose of this experiment was to measure the field gradient at different distances from the magnets in the on-axis (central) position.

Several conclusions can be made, which are completely consistent with known magnetic theory:

1. The magnetic field from a single magnet diminishes with increasing distance from its surface.
2. The magnetic field gradient is maximized near the magnet surface and diminishes with increasing distance from its surface.

The strongest usable field gradient is limited by the mechanical layout necessary to attract, hold, pull and finally release magnetic bead tagged DNA.

From these measurements it can approximated that the largest magnetic field gradient that can be generated using a small magnet is about 450 Tesla/m. This assumption is based on the practical assumption that a gap of at least 0.35 mm is required between the surface of the magnet and the magnetic beads being manipulated. Even so, such a small gap would not be easy to implement.

For a given magnetic field gradient the force on a magnetic bead F can be determined, at least approximately. Those calculation are explained in the copied section of the disclosure above. The calculations below estimate the force on a 1.05 μm Dynabead™—a commonly used bead for biological manipulation.

The magnetization calculations are presented in FIG. 21. The bead saturation magnetization value is taken from experiments in the thesis of Smistrup, 2007 entitled "Magnetic separation in microfluidic systems"

The bead size in this example calculation is about the largest that could be considered for reasons of economy and performance. Larger commercially available beads usually contain lower density magnetic material. Another consideration is that a thick coating may be required to insure separation of the magnetic beads such that they do not clump.

Electrical Forces in the Nanopore

If the effect of Brownian motion is to be minimized then maximizing the tension on DNA is advantageous. Obviously, this has practical limits such as the breaking force limit of DNA and the strength of the magnetic beads connection to the DNA, and electrical limitations. A commonly discussed nanopore bias voltage is 100 mV to 400 mV. The corresponding force on ssDNA is between 10 pN and 100 pN. The wide range is related to pore size and differing assumptions regarding the shielding effect of electro-osmatic flow. (i.e. the flow of positively charged ions in the opposite direction that the negatively charged ssDNA is pulled by the nanopore voltage bias.)

The calculated magnetic bead force, 8.18pN is therefore at the low end of this estimated range and may therefore present a practical challenge to implementing the method, at least without compromising the assumptions made.

Soft Magnetic Materials

Soft magnetic materials are loosely defined as those materials that are easily magnetized and demagnetized. They typically have intrinsic coercivity less than 1000 A/m. They are used primarily to enhance and/or channel the flux produced by an electromagnet or by a permanent magnet or other source.

The main material property often used as a figure of merit for soft magnetic materials, is the relative permeability which is a measure of how readily the material responds to the applied magnetic field.

Another desirable property is low coercivity, which is the tendency of a material to retain magnetic field after the magnetic flux source has been removed. Low coercivity is best for dynamic applications.

Another desirable property is high saturation magnetization which is the ability of the material to permit high magnetic flux intensities.

The reluctance of a material is inversely proportional to its permeability. Soft magnetic materials therefore have low-reluctance.

Magnetic Flux

Magnetic flux forms a closed loop between the opposing poles of a magnet (either permanent or electric), but the path it takes depends on the reluctance of the materials near it. In simplistic terms, magnetic flux tends to 'prefer' the route through low-reluctance materials. Air and water have much higher reluctance than soft magnetic materials. A soft magnetic structure positioned on a non-magnetic substrate or within a non-magnetic fluid or gas will therefore be an attractor for magnetic flux provided its geometry can form part of the flux path between the magnets poles.

The concentration of flux in and around the soft magnetic structures creates temporary poles to be formed. Since the magnetic flux becomes more concentrated approaching these poles from outside the force acting on magnetic beads is always attractive toward the soft magnetic structure. Changing the direction of the magnetic field that the soft magnetic structures are exposed to does not make the force repulsive.

Layout

The invention is illustrated in FIG. 3. This illustration contains many of the structures disclosed by PCT/US16/59794 Lei et al with a number of additions and changes.

The nanopore (500) is mounted in the nanopore chip (501) which separates a trans space (651) from a cis space (650). Both of these spaces are filled with an appropriate solution. An electrical potential or voltage bias (530) can be applied between the two spaces that are only connected via the nanopore (500). Separated from the nanopore chip (501) by a distance (571) and oriented substantially parallel to it is the scan plate (510). The side of the scan plate (510) facing the nanopore chip (501) includes one or more soft magnetic structures (511).

The DNA to be analyzed (600) is attached to a flexible linker molecule (602) which is further attached to a magnetic bead (620). During sequencing the assembly (600, 601, 602, 620) is pulled partially into the nanopore (500).

A controllable magnet (520) provides magnetic flux through the soft magnetic structures (511) and through the cis space (650) between the scan plate (510) and the nanopore chip (501). The lower surface of the controllable magnet is a distance (524) away from the surface of the scan plate of the scan plate (510) the faces the nanopore chip (501) and contains the soft magnetic structures (511). The magnetic flux (522) from the controllable magnet (520) diverges as it gets further away.

The term "controllable magnet" (520) is used broadly. The field strength and polarity of an electromagnet can be controlled simply by varying its driving current. If a permanent magnet is used then the field strength the soft magnetic structures are exposed to can be varied by altering the relative position of the permanent magnet and the soft magnetic structures. Another means of varying a permanent magnets field is by diverting the magnetic field along other paths using permeable materials. An assembly of permanent magnets such as a Halbach array could also be used to generate a very strong magnetic field. A pole-piece or other structure could be used to direct magnetic flux from a magnet to the scan plate or to control the magnetic flux.

In order to concentrate the magnetic flux the soft magnetic structures (511) must provide a low reluctance path that allows the flux to avoid passing through high reluctance material. It is advantageous for the magnetic structures to be long in the direction of the magnetic flux such that more high-reluctance material is avoided. The soft magnetic structures must have substantial gaps between them from which to draw flux from. Since all the magnetic flux passes between the poles of the controllable magnet the soft magnetic structures do not create flux but create the concentration by rearrangement.

Example #1—2d Analysis of Infinite Rectangles

For this analysis the magnetic finite element analysis program FEMM 4.2 by David Meeker was used.

Steel magnetic structures (1010 alloy) in a strong magnetic field were modeled and the resultant field analyzed. The analysis mode was 2 dimensional. This type of analysis is good for examining the flux around multiple bodies. This underestimates the flux concentration since magnetic flux is drawn from beside the 2d shape only.

The modeled layout is illustrated in FIG. 4. The permanent magnet is a Neodymium Iron Boron grade 52. (i.e. NdFeB-52). The magnet is 20 mm wide and 10 mm tall. The location of the soft magnetic structures is 4 mm below the lower pole, located on-axis. At this location the magnetic field has a strength of about 0.3 T (3000 Gauss). The field is slightly divergent at this location.

The soft magnetic structures are infinite rectangles, 1 μm wide×5 μm tall with 45 degree corners 0.1 μm in each direction. There are 4 structures on spacing of 5 μm center to center. (i.e. 4 μm gaps)

FIG. 5 shows the modeled magnetic flux near the soft magnetic structures and FIG. 6 is a close up on the immediate area around them. Although immediately near the ends of the soft magnetic structure the flux lines are redirected the effect is very localized. At 10 μm distance in any direction there is minimal distortion to the field.

FIG. 7 shows the flux lines as solid lines and the field strength as grayscales.

FIG. 8 is a graph of the magnetic field strength and field gradient along a line directly below the center of the bottom surface of one of the rectangular soft magnetic structures (3$^{rd}$ from the left).

At 1 μm the field gradient is 80000 Tesla/m, at 2 μm it is 20000 Tesla/m and at 3 μm it is about 7000 Tesla/m. These gradients are very large and therefore should hold magnetic beads with strong force.

The local region with strong forces is shown in FIG. 3 by dimension (523).

A little further away the field gradient is less as the local effect of the soft magnetic structures diminishes. There is still an attractive force, sufficient to pull magnetic beads toward the scan plate provided they are not under tension from the nanopore. Such is the condition when the distance between the nanopore chip and the scan plate is less the length of the linker molecule.

The local area, (523) is dominated by the flux concentration of the soft magnetic deposits. Further away the flux roughly corresponds to the original field of the permanent magnet as if the soft magnetic deposits were not present.

Example #2—Axially-Symmetric Analysis of a Cylinder

For this analysis, the magnetic element structure analysis program FEMM 4.2 by David Meeker was used. A single soft magnetic structure of permalloy in a strong magnetic field was modeled and the resultant field analyzed. The analysis mode 'axially-symmetric' in which modeled regions are defined in a 2d plane which is then swept about an axis. The analysis mode is truly 3d but limited to bodies symmetric about a single axis.

The physical layout is illustrated schematically in FIG. 9 and also in FIG. 10 as it was configured in the computational model.

The permanent magnet is type NdFeB-52 and has dimensions 20 mm diameter×10 mm height. The top of the soft magnetic structure is 4 mm from the bottom face of the permanent magnet. The soft magnetic structure dimensions are 2 μm diameter×5 μm height. The soft magnetic material used in the analysis was permalloy 87. The magnetic field strength near the soft magnetic structures is about 0.3 Tesla.

The magnetic flux predicted by the finite element analysis is shown in FIG. 10. For analytical purposes the software uses a series of shells around the modeling area to allow the flux exit and re-enter. This limits the computation to a finite area.

The axial-symmetric model is a 3d approach with the limitation that the physical model has one common axis of symmetry. Some of the results of the analysis are shown in FIG. 11. The corner of the cylinder was chamfered at 45 deg to avoid artifacts in the analysis. The flux lines are bent to follow the path through the soft magnetic structure from top to bottom.

The graph in FIG. 12 is of the magnetic field strength along a line directly below the center of the bottom surface the cylindrical soft magnetic structures. At 1 μm the field gradient is 130000 Tesla/m, at 2 μm it is 70000 Tesla/m and at 3 μm it is about 20000 Tesla/m. These gradients are very large and therefore should hold magnetic beads with strong force. The gradients are somewhat larger at the corresponding distances than those predicted for the infinite rectangles.
Zero Flux?

The soft magnetic structures are very effective at generating strong magnetic field gradients when placed in comparatively weak magnetic fields. In order to release magnetic beads that are held by these gradients it may be necessary to isolate the soft magnetic structures from magnetic fields.

It may also be necessary to shield the scan plate (510) and soft magnet structures (511) from the controllable magnet (520) when strong flux is not needed. This could be accomplished by moving the controllable magnet (520) some distance away and surrounding it by a cover of mu-metal or another suitable magnetic material such that magnetic flux has a substantial low reluctance route between its poles.

Another approach would be to shield the scan plate and other components from external magnetic fields from nearby equipment or even from the earth's magnetic field. A mu-metal shield can be used although this may need to be removed when the controllable magnet is brought close to avoid interference or a reduction of the flux.

It is possible that either the soft magnetic structures or the magnetic beads may retain some magnetic field. One method to eliminating this residual magnetism is to generate a magnetic field that changes direction numerous times while at the same time progressively decreasing in magnitude. This effectively scrambles the magnetic field in the exposed materials. This could be accomplished by an electromagnet driven with suitable electronic circuitry. It could also be accomplished by a rotating permanent magnet that is gradually moved away or gradually shielded to reduce its field intensity.
Soft Magnet Structures and Arrays The dimensions, layout and composition of the soft magnetic structures affect how they perform.

Layout

Many layouts of soft magnetic structures are possible, such as:

A solitary structure
  A grid array of structures
  A hexagonal array of structures
  A solitary strip
  A linear array of strips across an area
  The structures or groups of structures can be arranged in alignment with multiple nanopores on the nanopore chip. For example small arrays of structures can be positioned above each nanopore with gaps between the small arrays.
  A random pattern of structures The structures or groups of structures can be arranged in alignment with multiple nanopores on the nanopore chip. For example small arrays of structures can be positioned above each nanopore with gaps between the small arrays.

The structures can have different shapes such as:
  circular cylinders
  oval cylinders
  Rectangular Blocks
  Polygonal cylinders
  Pyramids
  Inverted pyramids
  Cones
  Inverted cones
  Elongated shapes
  Irregular particles
  Ridges Dimensions Diameter: A larger diameter soft magnetic structure will distort the magnetic flux further beyond its ends than a small diameter. The corresponding gradient may be smaller.

Height: The structure cannot be too short since it does not present a substantial low-reluctance 'short cut' for magnetic flux. Short structures do function, just not as efficiently as taller structures.

Spacing: Each structure draws flux from the area around it. (The area perpendicular to the flux direction). The structures cannot be too close together since that limits the magnetic field concentration. If the structures are too close it will also limit the range the field gradient is effective below the structure.

Composition: The ideal soft magnetic material has high permeability and low coercity. To have the maximum effectiveness the magnetic saturation must be such that all the magnetic flux from the 'draw area' can go through the structure. For example, a magnetic structure that has a cross-sectional area of 1 µm and a draw area of 10 µm and a magnetic saturation of 0.7 Tesla can fully accommodate all the flux from the draw area if the controllable magnets field is no more than 0.07 Tesla. The permeability is not solely determined by the composition but also the grain structure of the material.

Matching Soft Magnetic Structures to Magnetic Beads: The optimal size and spacing of a soft magnetic structure is related to the magnetic bead that the DNA is tagged with. A very small magnetic bead such as a 200 nm bead could be captured best by a soft magnetic of similar size since a very strong gradient could be generated which only penetrates a few hundred nm into the cis space. Similarly a very large magnetic bead such as a 20 micron bead would best be held by a larger soft magnetic structure such as a 20 micron diameter cylinder. This is a general rule for best results, but not a necessary condition because as long as the new magnetic field can generate sufficient force on the magnetic force, it will work.

Microfabrication

A particularly good fabrication method for the scan plate with soft magnetic structures is using micro-lithography. This has several benefits:

The substrate is a finely polished silicon or glass. This helps maintain the precise gap between the scan plate and the nanopore chip.
  Manufacturing methods are developed for creating patterns with micron or sub-micron accuracy.

FIG. 13 depicts a simplified example of a process for manufacturing the scan plate:

(a) Begin with a polished glass plate coated on one side with a conductive layer such as indium-tin-oxide. (ITO)
  (b) Coat the conducting side with a layer of photo-resist. The photoresist can be either positive or negative type. Negative is preferred since the UV light hardens it which has better stability.
  (c) Expose the photoresist with a chrome patterned mask. The wavelength of light must match the photoresist requirements, typically ultraviolet.
  (d) Positive photo resists are weakened by exposure and are subsequently dissolved in the exposed areas. Negative photoresists are stabilized in the exposed areas and the unexposed areas are subsequently dissolved away. The conductive layer is exposed in the desired pattern.
  (e) Electroplate the exposed patterned areas with a soft magnetic material such as permalloy. Permalloy is a metal alloy containing 80% nickel and 20% iron. A seed layer may be required to attain good adhesion to the conductive layer. The electrodeposition should be made sufficiently thick to lay flush or near-flush with the surface of the photoresist as shown.
  (f) Apply one or more protective coatings over the pattern. The protective coat(s) protects the pattern from exposure and may also minimize adhesion of magnetic beads.
  (g) (not shown) Dice (cut) the glass sheet into smaller scan plates.
  (h) (not shown) Clean the resulting "chips" to remove cutting debris.

Protruding Soft Magnetic Structures

The preceding examples and illustration have shown the soft magnetic structures to be flush with the scan plate surface or recessed. This is not essential. There may be advantages for the soft magnetic structures to protrude outward from the scan plate surface. The gaps between the soft magnetic structures could provide additional space for fluid to flow between the scan plate and the nanopore chip. The protruding soft magnetic structures could form ridges that span substantially across the scan plate with passages between.

FIG. 14 illustrates protruding soft magnetic structures. It may be more stable to make them wider at the base where they contact the scan plate substrate (513) than at the tips (see FIG. 14a). Such structures could be fabricated using an etching process where the tips of the structures are protected by a pattern of photoresist which is undercut as the soft magnetic material is etched away as in FIG. 14-b.

Procedure

PCT/US16/59794 Lei et al discloses an alignment procedure used to orient magnetic bead tagged DNA such that it can be pulled straight away from a nanopore. A very similar procedure can be applied to using the soft magnetic cores.

The steps below are designed to align ssDNA that has been tagged with a dsDNA linker and a magnetic bead:
1. The chamber on the cis side of the nanopore array is filled with a buffer solution containing the magnetic bead tagged DNA (as described above).
2. The nanopore bias voltage is set to draw the negatively charged DNA into the nanopore. The free end of the DNA (600) enters the nanopore (500). This can be detected by monitoring the nanopore open-pore current. The progress of the DNA molecule into the nanopore is stopped by the linker node which cannot enter the nanopore. A properly chosen linker node can also block other DNA from entering the nanopore.
3. Some tagged DNA samples will not occupy a nanopore and stay scattered on the nanopore chip surface or in the cis buffer reservoir. We term the tagged DNA inside a nanopore as "engaged" while the tagged DNA outside the pore "unengaged". It may be desirable to remove the unengaged DNA from the cis reservoir during the sequencing of the engaged DNA if interference is a concern. This can be accomplished by a wash step performed before applying the magnetic field. The unused DNA that is removed can be sequestered in a storage reservoir and released for a subsequent round of the sequencing process.
4. The scan plate (510) is brought relatively close to the nanopore surface, but with the separation (571) is larger than the longest linker molecule length. The controllable magnet is enabled. The magnetic beads are outside the reach of the strong gradients from the soft magnetic structures on the scan plate (510). The magnetic beads are affected by the far-field of the controllable magnet (520). $F_m$ is the magnetic force acting on the magnetic beads in suspension pulling toward the scan plate, $F_{es}$ the electric force acting on the unengaged DNA pulling toward the nanopore, and $F_{el}$ the electric force acting on the engaged DNA pulling them through the nanopore. The force in the nanopore, $F_{el}$ is several orders of magnitude larger than force on the unengaged DNA, $F_{es}$. By activating the adjustable magnet (520), starting with a zero or very weak magnetic field, and gradually increasing the magnetic field strength such that $F_{es} \ll F_m \ll F_{el}$ the magnetic force is sufficient to draw any remaining unengaged DNA to the scan plate but insufficient to pull engaged DNA out of the nanopores. The magnetic beads (620) linked to the engaged DNA will be drawn straight above the linker-node beads (603), extending (straightening) the DNA and aligning perfectly with the corresponding nanopore.
5. The scan plate is then lowered further to allow all magnetic beads corresponding to the engaged DNA to contact the scan plate directly above them. The magnetic beads are captured by the strong local magnetic gradients and are drawn laterally to the nearest soft magnetic structure. This may result in the magnetic bead being sli misaligned from the corresponding nanopore (discussed below).
6. After all the magnetic beads (620) are in contact, the magnetic field is increased to make the magnetic force $F_m$ much larger than the electric force $F_{el}$ on the engaged DNA ($F_m \gg F_{el}$). The magnetic beads (620) are pulled tightly against the scan plate (510), so that they track the motion of the scan plate precisely. The DNA can be sequenced as it goes in and out of the pore as many times as required by moving the scan plate (or by moving the nanopore substrate) at a precisely controlled speed. After the DNA is sequenced, the magnetic force can be turned off to release the tagged DNA and start another round of sequencing in a short time without changing buffer or additional sample processing. As noted above there may be a residual magnetic field that must be dispelled to release the magnetic beads.

Misalignment of Beads?

The soft magnetic structures individually create a concentration of magnetic flux. When fabricated in a repeating pattern on the scan plate the soft magnet structure create of pattern of locations that strongly attract magnetic beads when placed in magnetic field. The attraction points are discreet points separated by gaps (528) rather than a continuum across the scan plate. The maximum 'error' or 'misalignment' of the magnetic bead location (529) is approximately one-half the distance between the soft magnetic structures for a hexagonal pattern, and about 0.7 the spacing for a square grid. This is illustrated in FIG. 15.

Features on the order of 1-5 μm in size and spacing on the order of 3-10 μm seem appropriate for magnetic beads that typically have diameters in the range 50 nm-3 μm and linker lengths on the order of 10-30 μm. FIG. 22 presents the degree to which misalignment affects the rate at which the DNA strand is pulled out of the nanopore. The DNA motion is determined using simple geometric relationships. As the plate distance (571) is increased the motion of the DNA through the nanopore approaches the plate motion, i.e. 1 μm of DNA occurs for every 1 μm of plate displacement. This 'speed reduction factor was calculated with simple geometry and presented for various DNA lengths and misalignments in FIG. 22.

For example, consider a A-DNA is used as a double-stranded linker molecule. The un-stretched length of the linker molecule is about 16 μm. If the soft magnetic structures are fabricated on a 4 μm hexagonal pattern the maximum misalignment would be a little more than 2 μm. The corresponding motion would be about better than 0.99 μm/μm for the first bases and would improve as the distance increased. The DNA motion would be very linear with respect to the separation distance between the scan plate and the nanopore chip.

Alignment of Soft Magnet Material Structures to Multiple Nanopores

For many applications it may be advantageous to utilize a substrate comprising a plurality of nanopores. There may be utility limiting the areas of the scan plate on which the soft magnetic material structures are fabricated to only those areas directly above each nanopore. Such an arrangement would reduce consumption of the magnetic material and may hold other advantages. In the simplest case a solitary soft magnetic material structure could be fabricated directly above each nanopore. Such an arrangement would require careful alignment. It may be easier to fabricate an arrangement in which a cluster of soft magnetic structures is placed above each nanopore. This allows for some tolerance in the lateral positioning of the clusters.

FIG. 19 illustrates such an arrangement as it might be applied to a solid state nanopore substrate 755. A portion of this substrate 755 is shown. It depicts 4 nanopore locations 754. Each nanopore is centered in a thinned window 753. Superimposed above each nanopore is a hexagonal cluster of 19 soft magnetic material structures 752. For the purposes of illustration, the cluster and the nanopores are shown with some lateral misalignment.

Dynamic Chamber with Soft Magnetic Structures

PCT/US16/59794 Lei et al discloses a "dynamic chamber". This assembly largely consists of the a nanopore chip and scan plate which are coupled mechanically in a way that allows some relative movement of those structures. Assembling the nanopore chip and the scan plate in a small assembly can help reduce mechanical vibration by reducing the mechanical path length between them. This assembly also could be manufactured a disposable, single-use product which eliminates possible cross-contamination with DNA from sub-sequent measurements.

The assembly presented by PCT/US16/59794 Lei et al requires minimal modification to make use of soft magnetic structures: FIG. 16 illustrates this: Soft magnetic structures [511] are added to the bottom surface [515] of the scan plate [510]. It may be necessary to provide clearance [518] such that a controllable magnet can be positioned near the back side of the scan plate [510].

It should be noted that the composition of the assembly [580] should be such that it is not adversely affected by a strong magnetic field. This dictates that the for the most part materials that cannot be magnetized should be used in the disposable assembly.

Optical Separation Feedback

The microfabrication method described above can be used to create patterns of soft magnetic material on an otherwise transparent substrate. It may be possible to monitor the separation distance between the scan plate and the nanopore chip by imaging through the scan plate since light may be only partially obstructed. The soft magnetic structures typically occupy only a small fraction of the area of the scan plate. This can permit imaging through the scan plate to see the window of the nanopore chip. FIG. 17 illustrates this: The focal point of an imaging system indicated by the lens 700 can be moved up or down either by translating the lens as indicated by 701 or by moving the corresponding digital camera (not shown), a tube lens (not shown) or another optical element in the imaging system. By checking the focal position of the soft magnetic structures 511 on the scan plate 510 or another identifying feature on the scan plate 510 and comparing it to the focal position of the window 503 on the nanopore chip 501 the separation distance 571 can be determined.

Since the magnet 520 must occupy the location above the scan plate 510 during sequencing the optical system must be exchanged for the magnet 520 and vice versa.

The lens 700 or lens system must have sufficient working distance that the scan plate 510 and supporting structure do not physically interfere with it. Objective lenses with high numerical aperture and sufficient working distance are preferred. Using automated image analysis and a hill-climbing algorithm the sharpest focal plane could be determined even with relatively low numerical aperture objectives.

A transillumination light source 703 is illustrated.

FIG. 18 panels (a) and (b) are images recorded with a 20× objective lens with numerical aperture 0.4. These are images of the thinned silicon-nitride window of a solid state nanopore chip as seen through a scan plate with 4.5 µm permalloy structures in a hexagonal pattern with center to center spacing of 9 µm. The structure height is 8 µm. The bright square is the light passing through the window. The round shadows are where light is blocked by the soft magnetic structures on the scan plate. The images are recorded at heights 23 µm apart. Panel (a) is focused on the window edges. Panel (b) is focused on the tops of the permalloy structures. The implied separation distance from bottom of the structures is 15 µm. The white lines drawn through the images indicate the path of the intensity profiles shown in the corresponding panels (c) and (d).

For the window-focus image the edge transitions 710 and 711 are steeper and more well defined than in the core-focus image.

For the core-focus image the dips 712, 713, 714 are steeper and more flat-bottomed than in the window-focus image.

REFERENCES

United States patent application PCT/US16/59794, Lei, M., Roorda, R., Chen, Z., Ho, N., Wang, Y. "Methods and systems for controlling DNA, RNA and other biological molecules passing through nanopores"

Smistrup, K., Hansen, M. F., Bruus, H., Tang, P. T., & Kruhne, U. W. W. (2007). Magnetic separation in microfluidic systems.

Meeker, D. "Finite Element Method Magnetic", Software, version 4.2

Aspects of the Invention

It is an aspect of the present invention to provide a method of holding and pulling DNA tagged with magnetic beads.

It is an aspect of the present invention to provide a method to reduce the effect of Brownian motion on the progression of DNA through a nanopore by holding the one end of the DNA securely and thereby facilitating strong tension to be applied to the DNA.

It is an aspect of the present invention to provide a method of holding DNA tagged with magnetic beads against a scan plate with a strong retaining force.

It is an aspect of the present invention to provide a method of holding DNA tagged with magnetic beads against a scan plate such that sufficient retention force is achieved with sub-micron diameter magnetic beads.

It is an aspect of the present invention to provide a method of holding DNA tagged with magnetic beads against a scan plate such that sufficient retention force is achieved with magnetic beads with diameters equal or greater to one micron.

It is an aspect of the present invention to provide a method of holding DNA tagged with magnetic beads against a scan plate and that the DNA tagged with magnetic beads can rapidly be released from the scan plate.

It is an aspect of the present invention that the soft magnetic structures can be manufactured as part of a disposable device.

The invention claimed is:

1. A system for controlling movement of a charged molecule through a nanopore comprising;
   a) a substrate positioned to separate a cis space and a trans space;
   b) a charged molecule attached to a magnetic bead located in the cis space;
   c) a nanopore in the substrate through which at least a portion of the charged molecule can pass from the cis space to the trans space;
   d) an electrical potential source for applying a bias voltage between the cis space and the trans space;
   e) a scan plate located in the cis space and placed substantially parallel to the substrate;
   f) a magnet or an assembly of magnets configured to create a magnetic field that passes through the scan plate;

g) a microfabricated structure comprising a soft magnetic material on or near a surface of the scan plate facing the nanopore, wherein the microfabricated structure is configured to match the magnetic bead in size and configures the magnetic field to create a localized magnetic field gradient; and h) an actuator coupled to the scan plate for controlling the distance between the substrate and the scan plate, wherein the actuator allows for nanometer precision movement of the scan plate.

2. The system of claim 1, wherein magnitude and/or direction of the magnetic field through the scan plate are controlled by a controller and wherein the magnet or the assembly of magnets is selected from the group consisting of an electromagnet, an adjustable permanent magnet, a group of magnets, or a combination thereof.

3. The system of claim 1, wherein a portion of the magnetic field passes through the scan plate and wherein a direction of the portion of the magnetic field passing through the scan plate surface is substantially normal to the scan plate surface facing the substrate.

4. The system of claim 1, wherein the local magnetic field gradient created by the microfabricated structure pulls the magnetic bead towards the microfabricated structure and holds the magnetic bead on the scan plate with a force magnitude that exceeds the electrostatic force of the voltage biased nanopore acting on the charged molecule.

5. The system of claim 1, wherein the scan plate with a plurality of microfabricated structures is sufficiently transparent to allow for an optical imaging system to resolve features on the substrate behind the scan plate.

6. The system of claim 1, wherein the microfabricated structure on the scan plate has a layout selected from the group consisting of a solitary structure, a grid array, a hexagonal array, a solitary strip, a linear array of strips across an area, a patterned array of clusters of structures, a random pattern of structures, and a combination thereof.

7. The system of claim 1, wherein the microfabricated structure or a cluster of microfabricated structures on the scan plate aligns with the nanopore on the substrate.

8. The system of claim 1, wherein a plurality of microfabricated structures or a plurality of clusters of microfabricated structures on the scan plate align with a plurality of nanopores on the substrate.

9. The system of claim 1, further comprising an adjustment stage with micrometer precision that is coupled to the scan plate or coupled to the substrate, wherein the adjustment stage is configured to move an object laterally and/or vertically for pre-sequencing position adjustment.

10. The system of claim 1, wherein the microfabricated structure has a shape selected from the group consisting of a circular cylinder, an oval cylinder, a rectangular block, a polygonal cylinder, a pyramid, an inverted pyramid, a cone, an inverted cone, an elongated shape, an irregular particle, a ridge, and a combination thereof.

11. The system of claim 1, wherein the material for the microfabricated structure is selected from the group consisting of:
 a. a permalloy;
 b. a nickel-iron-molybdenum alloy;
 c. a nickel-iron alloy comprising greater than about 40% but less than about 75% nickel;
 d. a nickel-iron alloy comprising equal or greater than about 75% but less than about 85% nickel;
 e. a nickel-iron alloy comprising equal or greater than about 85% nickel;
 f. a substantially pure nickel;
 g. a substantially pure iron;
 h. a nickel-cobalt alloy;
 i. an iron-nickel-cobalt alloy; and
 j. an iron-silicon alloy.

12. The system of claim 1, comprising a plurality of microfabricated structures, having a center-to-center spacing between about 3 to 10 microns.

13. The system of claim 1, comprising a plurality of microfabricated structures, having a center-to-center spacing selected from the group consisting of:
 a. about 250 nanometers to about 1 micron;
 b. about 1 micron to about 3 microns; and
 c. about 10 microns to about 40 microns.

14. The system of claim 1, where the microfabricated structure's diameter is selected from the group consisting of:
 a. about 100 to 500 nanometers;
 b. about 500 to 1500 nanometers;
 c. about 1.5 microns to 5 microns; and
 d. about 5 microns to 20 microns.

15. The system of claim 1, wherein the substrate is a nanopore chip comprising a plurality of nanopores positioned in a planar arrangement wherein each nanopore is substantially equidistant from the facing surface of the scan plate.

16. The system of claim 1, wherein the magnetic bead is comprised of material with a magnetic property selected from the group consisting of: (a) paramagnetic; (b) superparamagnetic; (c) ferromagnetic; and a combination thereof.

17. The system of claim 1
 wherein the charged molecule is a nucleic acid sequence, a polypeptide sequence, or a combination thereof; and
 wherein the nucleic acid sequence is selected from the group consisting of single stranded DNA; double stranded DNA; single stranded RNA; oligonucleotide; a sequence comprising a modified nucleotide; and a combination thereof.

18. The system of claim 1, wherein the nanopore has a shape selected from the group consisting of:
 a. a circle;
 b. a slit;
 c. a rectangle;
 d. an irregular shape; and
 e. an oval.

19. The system of claim 1 further comprising
 a detector for determining an identity or a characteristic of an individual base unit of the charged molecule as it passes through the nanopore, wherein the base unit of the charged molecule is measured by ionic current blockage, recognition tunneling, field-effect transistor, other base sensing methods, or a combination thereof.

20. The system of claim 1, wherein the actuator comprises a precision linear motion stage configured to control the distance between the scan plate and the substrate such that the charged molecule can be pulled out or inserted into the nano pore at a steady rate providing accurate base unit sequencing of the charged molecule.

21. The system of claim 20, wherein a rate of travel of the charged molecule through the nanopore is about 0.25 ms per base unit or slower.

22. The system of claim 20, wherein a rate of travel of the charged molecule through the nanopore is from about 5 ms to about 20 ms per base unit.

23. The system of claim 1, further comprises a flexible linker molecule disposed between the magnetic bead and the charged molecule, wherein one end of the linker is attached to the first end of the charged molecule and other end of the linker is attached to the magnetic bead.

24. The system of claim 23, wherein the flexible linker molecule is selected from the group consisting of a single stranded nucleic acid; a double stranded nucleic acid; a polypeptide chain; a cellulose fiber or any flexible linear polymer, either natural, modified or synthesized; and a combination thereof.

25. The system of claim 23, wherein the flexible linker molecule is the same kind of molecule as the charged molecule.

26. The system of claim 23, further comprises a linker node which is disposed between the flexible linker molecule and the charged molecule and wherein the linker node is configured to block the linker molecule from entering the nanopore.

27. The system of claim 26, wherein the linker node is selected from the group consisting of an antibody, an enzyme, a NeutrAvidin, a streptavidin, and an avidin, or a polymer complex, or a particle or a bead, or a combination thereof.

28. A method for pulling a charged molecule through a nanopore comprising:
   a. attaching at least one charged molecule to at least one magnetic bead;
   b. allowing a charged molecule to be partially pulled into a nanopore in a substrate positioned to separate a cis space and a trans space, using a bias voltage applied between the cis space and the trans space by an electrical potential source;
   c. superimposing a strong magnetic field onto a scan plate thereby generating a strong magnetic field gradient in close proximity to a microfabricated structure comprising a soft magnetic material that is built onto the scan plate;
   d. holding the magnetic bead tightly against the scan plate inside the strong magnetic gradient region in the vicinity of the microfabricated structure; and
   e. moving the scan plate away from or toward the nanopore with nanometer precision using an actuator coupled to the scan plate, and thereby concurrently moving the magnetic bead with nanometer precision and thereby moving a portion of the charged molecule through the nanopore with nanometer precision.

29. The method of claim 28 in which the strong magnetic field is created by:
   a. a controllable electromagnet; and/or
   b. a movable permanent magnet.

30. The method of claim 28 further comprising detecting an identity or a characteristic of an individual base unit of the charged molecule as it passes through the nanopore, wherein the base unit of the charged molecule is detected by ionic current blockage, or recognition tunneling, or field-effect transistor, or other base sensing methods, or a combination thereof.

31. The method of claim 30, wherein passing the charged molecule through the nanopore comprises moving the scan plate away from or towards the substrate.

* * * * *